United States Patent
Sim et al.

(10) Patent No.: US 9,568,434 B2
(45) Date of Patent: Feb. 14, 2017

(54) GEMSTONE TESTER AND A METHOD OF CHARACTERISING A GEMSTONE

(71) Applicant: Presidium Instruments Pte Ltd., Singapore (SG)

(72) Inventors: Hwa San Sim, Singapore (SG); Joanne Yeo, Singapore (SG)

(73) Assignee: Presidium Instruments Pte Ltd, Singapore (SG)

( * ) Notice: Subject to any disclaimer, the term of this patent is extended or adjusted under 35 U.S.C. 154(b) by 0 days.

(21) Appl. No.: 14/429,319

(22) PCT Filed: Oct. 3, 2013

(86) PCT No.: PCT/SG2013/000430
§ 371 (c)(1),
(2) Date: Mar. 18, 2015

(87) PCT Pub. No.: WO2014/055041
PCT Pub. Date: Apr. 10, 2014

(65) Prior Publication Data
US 2015/0219567 A1   Aug. 6, 2015

Related U.S. Application Data

(60) Provisional application No. 61/709,310, filed on Oct. 3, 2012.

(51) Int. Cl.
*G01N 21/00* (2006.01)
*G01N 21/87* (2006.01)

(52) U.S. Cl.
CPC ......... *G01N 21/87* (2013.01); *G01N 2201/126* (2013.01)

(58) Field of Classification Search
CPC ......... G01N 21/87; G01N 21/88; G01N 21/17
See application file for complete search history.

(56) References Cited

U.S. PATENT DOCUMENTS 3,867,032 A * 2/1975 Bruck ................. G01N 33/381
356/30
4,907,875 A * 3/1990 Bowley ................. G01N 21/87
209/581
5,811,824 A    9/1998 Smith et al.
(Continued)

FOREIGN PATENT DOCUMENTS

WO   WO9116617 A1   10/1991

OTHER PUBLICATIONS

International Search Report dated Dec. 4, 2013 and International Preliminary Report on Patentability dated Feb. 23, 2015 corresponding to PCT/SG2013/000430, 9 pages.

*Primary Examiner* — Kara E Geisel
*Assistant Examiner* — Maurice Smith
(74) *Attorney, Agent, or Firm* — Kilpatrick Townsend & Stockton LLP

(57) ABSTRACT

A gemstone tester for characterizing a gemstone and a method of characterizing a gemstone are provided, the gemstone tester comprising a detector unit for detecting one or more transmittances of the gemstone; and a processing unit for determining a first parameter based on one or more of the transmittances of light; and for characterizing the gemstone based on the first parameter; wherein each transmittance of the gemstone is a fraction of light of a specific wavelength that is passed through the gemstone.

22 Claims, 16 Drawing Sheets

(56) References Cited

U.S. PATENT DOCUMENTS

| | | | |
|---|---|---|---|
| 5,835,200 A | 11/1998 | Smith et al. | |
| 5,835,205 A | 11/1998 | Hunter et al. | |
| 6,980,283 B1 * | 12/2005 | Aggarwal | G01N 21/87 356/30 |
| 2006/0152729 A1 * | 7/2006 | Drennen, III | G01N 21/39 356/432 |

* cited by examiner

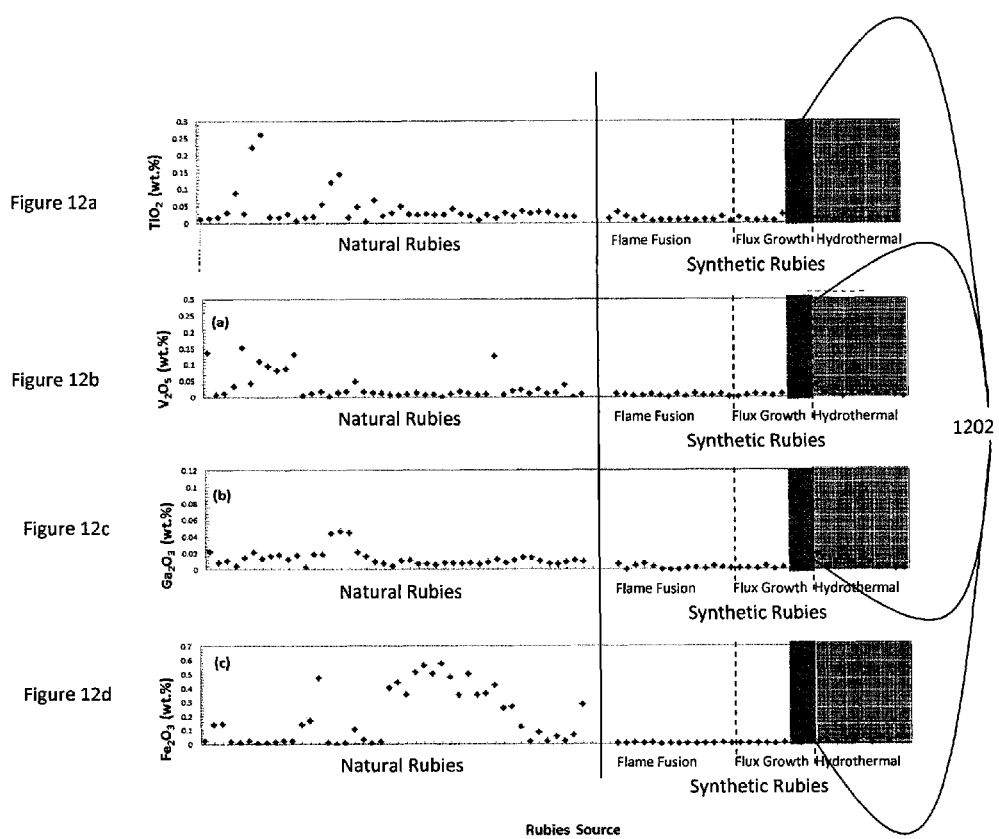

GEMSTONE TESTER AND A METHOD OF CHARACTERISING A GEMSTONE

TECHNICAL FIELD

The present invention relates broadly to a gemstone tester for characterising a gemstone, and to a method of characterising a gemstone.

BACKGROUND

Rare or precious gemstones have long been valued and sought after. Gemstones can include diamonds, rubies, sapphires, colour stones etc. Scientific advances have resulted in synthetic gemstones which are very similar to natural gemstones. In particular, synthetic gemstones may have crystal structures, chemical compositions, and other physical properties which are very similar to their naturally occurring counterparts. As such, the identification of natural gemstones from synthetic ones has been a challenge for gemstone traders.

There are several existing methods for identifying gemstones. For example, to identify synthetic rubies, microscopic visual observations and chemical analysis can be performed. Microscopic observations involve the use of a microscope to visually look for specific inclusions which characterize a natural ruby. Chemical analysis involves the use of specialized and sophisticated equipment such as one which employs X-ray spectrometers which utilize the methods of X-ray irradiation to determine the chemical composition of the gemstone.

However, the existing approaches for identifying gemstones are typically problematic. For example, microscopic visual observations require highly trained specialized personnel in order to spot and identify the specific inclusions. Even for highly trained personnel, such specific inclusions are difficult to be correctly identified or spotted. Thus, the method is extremely time consuming and prone to human errors.

The chemical analysis method requires the use of sophisticated equipment which also requires highly specialized training in order to operate the equipment. In addition, the equipment is typically bulky e.g. desk-bound and/or room sized, and therefore not easily portable for use at e.g. a gem trader's establishment or the like. Further, such equipment are typically not cost effective.

Therefore, there exists a need for a gemstone tester for characterising a gemstone, and for a method of characterising a gemstone, that seek to address or ameliorate at least one of the above problems.

SUMMARY

In accordance with one aspect, there is provided a gemstone tester for characterising a gemstone, the gemstone tester comprising: a detector unit for detecting one or more transmittances of the gemstone; and a processing unit for determining a first parameter based on one or more transmittances of light; and for characterising the gemstone based on the first parameter; wherein each transmittance of the gemstone is a fraction of light of a specific wavelength that is passed through the gemstone.

The gemstone tester may further comprise a light source unit for providing each specific wavelength of light.

The light source unit may comprise a plurality of LEDs (Light Emitting Diodes), each LED suitable for providing each of the specific wavelengths of light.

The light source unit may comprise a light source and a plurality of optical filters, the light source suitable for providing each of the specific wavelengths of light via the plurality of optical filters.

The light source unit may further comprise a light source holder for positioning the light source unit such that the detector unit is capable of detecting the transmittances of the gemstone.

The light source holder may further comprise directing means to direct the specific wavelengths of light at the detector unit.

The processing unit may further comprise controller means for controlling the light source unit to provide the specific wavelengths of light in sequence, said detector unit suitable for detecting the plurality of transmittances of the gemstone in sequence.

The first parameter may be determined by forming a relationship to one or more of the detected plurality of transmittances of light.

The relationship may be one or more of a group consisting of a addition, subtraction, multiplication, or division, of a first transmittance of light.

The processing unit may further comprise a storage memory for storing one or more threshold values; such that the processing unit is arranged to characterise the gemstone based on the first parameter in comparison with one of the threshold values.

The processing unit may be further capable of determining a second parameter based on two or more of the plurality of transmittances of light; and may be further capable of characterising the gemstone based on the first and second parameters.

The second parameter may be determined by forming another relationship to two or more of the detected plurality of transmittances of light.

The relationship may be one or more of a group consisting of a addition, subtraction, multiplication, or division, of a first transmittance of light; and the other relationship may be one or more of a group consisting of a ratio, addition, subtraction, multiplication, or division, between a second and a third transmittance of light.

The processing unit may further comprise a storage memory for storing one or more threshold values; wherein the processing unit is arranged to characterise the gemstone based on the first and second parameters in comparison with one or more of the threshold values.

The detector unit may be a photo diode.

The gemstone tester may further comprise one or more indicators for indicating a status of the tester, based on the characterisation of the gemstone.

The gemstone tester may further comprise a power unit for providing portable electrical power to the gemstone tester.

The gemstone may be one of a group consisting of rubies, diamonds, sapphires, and emeralds.

In accordance with another aspect, there is provided a method of characterising a gemstone, the method comprising: detecting one or more transmittances of the gemstone with a detector unit; determining a first parameter based on the one or more transmittances of light with a processing unit; and characterising the gemstone based on the first parameter with the processing unit; wherein each transmittance of the gemstone is a fraction of light of a specific wavelength that is passed through the gemstone.

The method may further comprise providing each specific wavelength of light with a light source unit.

The light source unit may comprise a plurality of LEDs (Light Emitting Diodes), such that the step of providing each specific wavelength of light is performed by each of the plurality of LEDs.

The light source unit may comprise one light source and a plurality of optical filters; such that the step of providing each specific wavelength of light is performed by switching the plurality of optical filters.

The method may further comprise positioning the light source unit with a light source holder such that the detector unit is capable of said detecting the transmittances of the gemstone.

The method may further comprise directing the specific wavelengths of light at the detector unit with directing means comprised in the light source holder.

The method may further comprise controlling the light source unit to provide the specific wavelengths of light in sequence, and controlling the detector unit to detect the plurality of transmittances of the gemstone in sequence.

The step of determining the first parameter based on one or more transmittances of light with a processing unit may comprise forming a relationship based on one or more of the detected plurality of transmittances of light.

The relationship may be one or more of a group consisting of a addition, subtraction, multiplication, or division, of a first transmittance of light.

The step of characterising the gemstone based on the first parameter with the processing unit may comprise comparing the first parameter with one threshold value stored in a storage memory of the processing unit.

The method may further comprise determining a second parameter based on two or more of the transmittances of light; and characterising the gemstone based on the first and second parameters.

The step of determining the second parameter may comprise forming an other relationship to two or more of the detected plurality of transmittances of light.

The relationship may be one or more of a group consisting of a addition, subtraction, multiplication, or division, of a first transmittance of light; and the other relationship may be one or more of a group consisting of a ratio, addition, subtraction, multiplication, or division, between a second and a third transmittance of light.

The step of characterising the gemstone may comprise comparing the first and second parameters with one or more of the threshold values stored in a storage memory of the processing unit.

The detector unit may be a photo diode.

The method may further comprise indicating a status of the tester with one or more indicators, based on the characterisation of the gemstone.

The gemstone may be one of a group consisting of rubies, diamonds, sapphires, and emeralds.

In accordance with yet another aspect, there is provided a non-transitory computer readable storage medium, having stored thereon computer code for instructing a processing unit to execute a method of characterising a gemstone, the method comprising: detecting one or more transmittances of the gemstone with a detector unit; determining a first parameter based on the one or more transmittances of light; and characterising the gemstone based on the first parameter; wherein each transmittance of the gemstone is a fraction of light of a specific wavelength that is passed through the gemstone.

The method may further comprise controlling a light source unit to provide the specific wavelengths of light in sequence, and controlling the detector unit to detect the plurality of transmittances of the gemstone in sequence.

The step of determining the first parameter based on one or more transmittances of light may further comprise forming a relationship between one or more of the detected plurality of transmittances of light.

The relationship may be one or more of a group consisting of a addition, subtraction, multiplication, or division, of a first transmittance of light.

The step of characterising the gemstone based on the first parameter with the processing unit may comprise comparing the first parameter with one threshold value stored in a storage memory of the processing unit.

The method may further comprise determining a second parameter based on two or more of the plurality of transmittances of light; and characterising the gemstone based on the first and second parameters.

The step of determining the second parameter may comprise forming an other relationship to two or more of the detected plurality of transmittances of light.

The relationship may be one or more of a group consisting of a addition, subtraction, multiplication, or division, of a first transmittance of light; and the other relationship may be one or more of a group consisting of a ratio, addition, subtraction, multiplication, or division, between a second and a third transmittance of light.

The step of characterising the gemstone may comprise comparing the first and second parameters with one or more of the threshold values stored in a storage memory of the processing unit.

BRIEF DESCRIPTION OF THE DRAWINGS

Example embodiments of the invention will be better understood and readily apparent to one of ordinary skill in the art from the following written description, by way of example only, and in conjunction with the drawings, in which:

FIGS. 12a to 12d show the chemical analysis of each of the sampled rubies for Titanium, Vanadium, Gallium and Iron additives respectively.

DETAILED DESCRIPTION

Figure 1A:
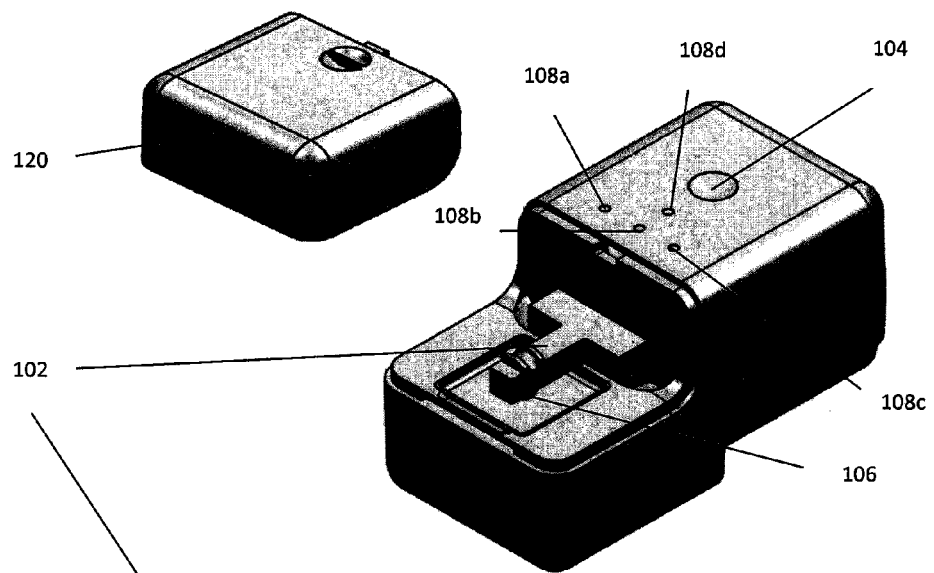
FIGS. 1a and 1b are perspective views of a gemstone tester in an example embodiment.

Example embodiments described herein may provide a gemstone tester for characterising a gemstone. The gemstone tester comprises a detector unit for detecting one or more transmittances of the gemstone; and a processing unit for determining a first parameter based on the plurality of transmittances of light. The processing unit further performs characterising of the gemstone based on the first parameter. Each transmittance of the gemstone is a fraction of light of a specific wavelength that is passed through the gemstone.

Example embodiments described herein may also provide a method of characterising a gemstone. The method comprises detecting one or more transmittances of the gemstone with a detector unit; determining a first parameter based on the plurality of transmittances of light with a processing unit; and characterising the gemstone based on the first parameter with the processing unit; wherein each transmittance of the gemstone is a fraction of light of a specific wavelength that is passed through the gemstone.

Example embodiments described herein may further provide a non-transitory computer readable storage medium, having stored thereon computer code for instructing a processing unit to execute a method of characterising a gemstone. The method may comprise: detecting one or more transmittances of the gemstone with a detector unit; determining a first parameter based on the plurality of transmittances of light; and characterising the gemstone based on the first parameter; wherein each transmittance of the gemstone is a fraction of light of a specific wavelength that is passed through the gemstone.

In the description, references to "characterising" broadly includes determining whether a gemstone is synthetic. In some example embodiments, characterising further includes identifying one or more properties of a gemstone.

In the description, references to "transmittance" of a gemstone should be understood to also relate inversely to the absorption property of the gemstone as understood by a person skilled in the art.

The terms "coupled" or "connected" as used in this description are intended to cover both directly connected or connected through one or more intermediate means, unless otherwise stated.

The description herein may be, in certain portions, explicitly or implicitly described as algorithms and/or functional operations that operate on data within a computer memory or an electronic circuit. These algorithmic descriptions and/or functional operations are usually used by those skilled in the information/data processing arts for efficient description. An algorithm is generally relating to a self-consistent sequence of steps leading to a desired result. The algorithmic steps can include physical manipulations of physical quantities, such as electrical, magnetic or optical signals capable of being stored, transmitted, transferred, combined, compared, and otherwise manipulated.

Further, unless specifically stated otherwise, and would ordinarily be apparent from the following, a person skilled in the art will appreciate that throughout the present specification, discussions utilizing terms such as "scanning", "calculating", "determining", "replacing", "generating", "initializing", "outputting", and the like, refer to action and processes of an instructing processor/computer system, or similar electronic circuit/device/component, that manipulates/processes and transforms data represented as physical quantities within the described system into other data similarly represented as physical quantities within the system or other information storage, transmission or display devices etc.

The description also discloses relevant device/apparatus for performing the steps of the described methods. Such apparatus may be specifically constructed for the purposes of the methods, or may comprise a general purpose computer/processor or other device selectively activated or reconfigured by a computer program stored in a storage member. The algorithms and displays described herein are not inherently related to any particular computer or other apparatus. It is understood that general purpose devices/machines may be used in accordance with the teachings herein. Alternatively, the construction of a specialized device/apparatus to perform the method steps may be desired.

In addition, it is submitted that the description also implicitly covers a computer program, in that it would be clear that the steps of the methods described herein may be put into effect by computer code. It will be appreciated that a large variety of programming languages and coding can be used to implement the teachings of the description herein. Moreover, the computer program if applicable is not limited to any particular control flow and can use different control flows without departing from the scope of the invention.

Furthermore, one or more of the steps of the computer program if applicable may be performed in parallel and/or sequentially. Such a computer program if applicable may be stored on any computer readable medium. The computer readable medium may include storage devices such as magnetic or optical disks, memory chips, or other storage devices suitable for interfacing with a suitable reader/general purpose computer. In such instances, the computer readable storage medium is non-transitory. Such storage medium also covers all computer-readable media e.g. medium that stores data only for short periods of time and/or only in the presence of power, such as register memory, processor cache and Random Access Memory (RAM) and the like. The computer readable medium may even include a wired medium such as exemplified in the Internet system, or wireless medium such as exemplified in bluetooth technology. The computer program when loaded and executed on a suitable reader effectively results in an apparatus that can implement the steps of the described methods.

The example embodiments may also be implemented as hardware modules. A module is a functional hardware unit designed for use with other components or modules. For example, a module may be implemented using digital or discrete electronic components, or it can form a portion of an entire electronic circuit such as an Application Specific Integrated Circuit (ASIC). A person skilled in the art will understand that the example embodiments can also be implemented as a combination of hardware and software modules.

Additionally, when describing some embodiments, the disclosure may have disclosed a method and/or process as a particular sequence of steps. However, unless otherwise required, it will be appreciated the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Figure 1B:
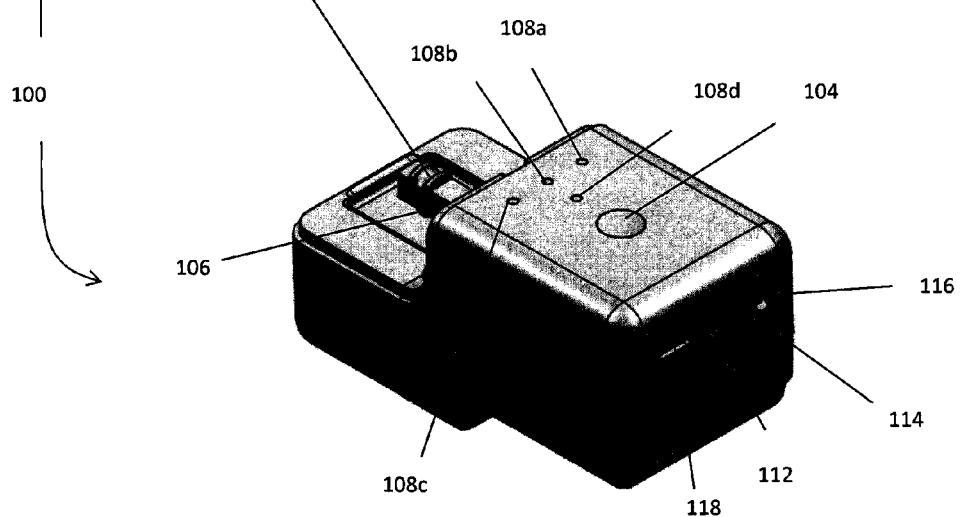

FIGS. 1a and 1b show perspective views of a gemstone tester 100 in an example embodiment. The gemstone tester 100 comprises a light source module 102 which comprises a plurality of light sources e.g. 106, and a detector module (not shown) which comprises a photo detector (not shown). The photo detector is positioned relative to the light source such that it is capable of receiving light emitted from the light source after passing through a gemstone under test. In the example embodiment, the photodetector is placed directly beneath the light source.

The gemstone tester 100 further comprises a cover 120 (not shown in FIG. 1b) for shielding a test area. The cover 120 is removable from the gemstone tester 100 to allow access to the test area, for e.g. the placement or removal of a gemstone for test; or replacement of the light source module 102. When the gemstone tester 100 is in use, i.e. a gemstone is under test, the cover 120 shields the test area from ambient light. This can prevent the photo detector (not shown) in the detector module from being affected by ambient light noise. The cover 120 may also serve to shield a user of the gemstone tester 100 from the light source e.g. 106, when the light source e.g. 106 emits hazardous light, such as light in the UV (Ultra Violet) range. The cover 120 is preferably made of, or comprises, substantially opaque material which can provide adequate shielding from external or ambient light. It will be appreciated to a person reading the present disclosure that while the cover 120 is shown to be removable or detachable, other variations where access to the test area is provided may also be allowed. For example, the cover may also be attached to the gemstone tester via a hinge to allow the cover to open or close around the test area.

The gemstone tester 100 further comprises a set of indicators 108a-108d. In the example embodiment, the indicators 108a-108d are visual indicators in the form of LEDs (light emitting diodes). The indicators indicate the results of a test (or characterization of a gemstone) conducted by the gemstone tester 100. In the example embodiment, indicator 108a may be a green LED which, when lit, indicates that the gemstone under test is a possible-natural gem. In one embodiment, the gemstone tester may conduct two different procedures to determine if the gemstone under test is a natural gem. In such an embodiment, the green LED may be lit to indicate that a first procedure is completed, and that the gemstone tester is ready and may commence with a second procedure e.g. once input is received from the user. Indicator 108b may be a red LED which, when lit, indicates that the gemstone under test is a synthetic gem. Indicator 108c may be a yellow LED which, when lit, indicates that the test was not successfully conducted and that further tests may be needed to ascertain if the gem under test is a natural or synthetic gem. Alternatively, indicator 108c may be a yellow LED which, when lit, indicates that the gemstone test procedure(s) was not correctly carried out and that the test with the gemstone tester should be repeated. In addition, the indicators may indicate a status of the gemstone tester 100. In the example embodiment, status indicator 108d may be an LED which, when lit, indicates that the gemstone tester is performing testing. That is, the status indicator 108d may serve to indicate that the light source 106 is turned on and is performing the test. Based on the status indication, a user operating the gemstone tester 100 may be aware the cover 120 is to be kept closed. Alternatively, the status indicator may indicate that the gemstone tester 100 is ready for tests.

It will be appreciated that while example embodiments show the use of LEDs for providing indications to the user on the result of the test conducted by the gemstone tester 100, as well as the status of the gemstone tester 100, any other means which can provide indications to the user may also be possible. The indications may be audio or visual. For example, the gemstone tester may be configured to play a particularly toned "beep" depending on the result of the test. Alternatively, the gemstone tester may use other types of light sources for providing the visual indication. In a further alternative, a LED or LCD display may also be incorporated to provide the visual indication.

In the example embodiment, the gemstone tester 100 further comprises a test button 104. When actuated by a user, the test button 104 triggers the start of the test by e.g. the microcontroller or microprocessor module/unit (not shown).

The gemstone tester 100 further comprises a power button 112 (not shown in FIG. 1a) which, when actuated by a user, allows the gemstone tester 100 to be powered on or off. The gemstone tester 100 is substantially a handheld device which may be powered by an internal energy/power source. Powering off the gemstone tester 100 may allow the energy source to retain its energy capacity for a longer period. When the gemstone tester 100 is powered on, a power indicator 114 in the form of e.g. a LED is lit to indicate this powered status.

The gemstone tester 100 further comprises a power jack connector 116 which allows an external power source (not shown) to be connected to the gemstone tester 100. For example, the gemstone tester 100 further comprises an adaptor module for converting an external power source e.g. an AC (Alternating Current) main line power source, for use by the gemstone tester 100.

The gemstone tester 100 further comprises a data connector 118 which allows data to be transferred between the gemstone tester 100 and an external processing device such as a portable tablet or desktop computer. The connector 118 is not limited to a USB (universal serial bus) connector as shown and may include, but is not limited to, e.g. Firewire, Ethernet, Thunderbolt, etc. The data connector 118 is also not limited to wired connections, and may include a wireless connection means.

Figure 2:
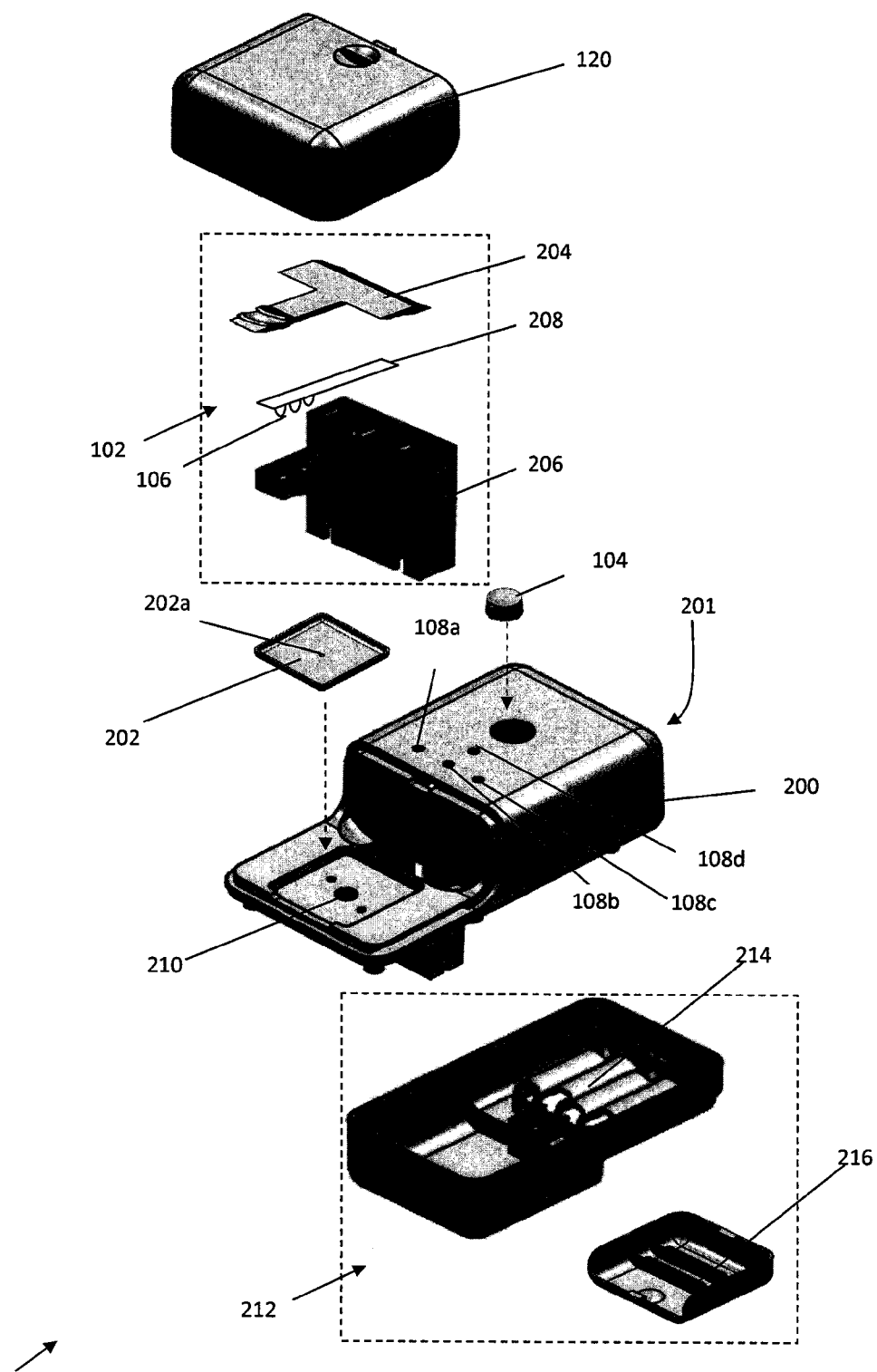
FIG. 2 is an exploded view of a gemstone tester in an example embodiment.

FIG. 2 shows an exploded view of the gemstone tester 100. The gemstone tester 100 comprises a main body 200. The indicators 108a-108d, test button 104, power button 112, power indicator 114, power jack connector 116, and data connector 118 as described with reference to FIGS. 1(a) and (b) are formed on the exterior of the main body 200. The power button 112, power indicator 114, power jack connector 116, and data connector 118 are formed on a rear end 201 of the main body 200, and are not visible in FIG. 2.

The main body 200 houses internally electronic circuitry in the form of e.g. one or more electrical components such as a microcontroller unit, memory units/modules, which are connected via printed circuit boards (PCBs) (not shown). In the example embodiment, the microcontroller unit (MCU) controls the indicators 108a-108d. In the example embodiment, the indicators 108a-108d are LEDs which are mounted on a printed circuit board to which the MCU is also connected. The printed circuit board is mounted against the top internal surface of the main body 200, such that the indicators 108a-108d are visible from outside of the main body 200, through associated apertures or windows in the main body 200.

The main body 200 further comprises an aperture in which the test button 104 can be inserted such that the test button 108 is mechanically coupled to the electronic circuitry such as the printed circuit board mentioned in the preceding paragraph housed within the main body 200. When coupled to the electronic circuitry, the test button 104 may serve to trigger the start of a test by the MCU which may further turn on or off the light sources e.g. 106 (FIG. 1a) in the light source module 102.

The main body 200 also comprises, internally, a detector module (not shown) controlled by the electronic circuitry also housed within the main body 200. A photo detector (not shown) of the detector module may detect light which passes through the aperture 210 on the main body.

The main body 200 further comprises a removable tray 202. The tray 202 comprises an aperture 202a that is smaller than aperture 210 provided on the main body 200. A gemstone may be first placed on aperture 202a of the tray 202, before the tray 202 is moved onto a docking area for receiving the tray 202 onto the main body 200. When the tray 202 is docked on the main body 200 (as shown in e.g. FIG. 1a), the aperture 202a of the tray 202 and the aperture 210 on the main body 200 are aligned, such that light from above the gemstone may pass through both apertures 202a and 210 to arrive at the photodetector (not shown) housed within the main body 200.

The light source module 102 comprises a light source holder 206, a light source PCB 208 and a light source plunger 204. The light source PCB 208 is housed within the light source holder 206 and is covered by the light source cover 204 when the light source module 102 is assembled (as shown in FIG. 1a). The light source module 102 can be inserted into a slot in the main body 200 such that the light source module 102 is coupled to the main body 200 (as shown in FIG. 1a).

The light source PCB 208 comprises a plurality of light sources e.g. 106 such as e.g. LEDs which are mounted and electrically connected to the circuitry on the PCB 208. When the light source module 102 is coupled to the main body 200, the light source PCB 208 is also electrically connected to the PCBs housed within the main body 200 described above. Operation of the light sources e.g. 106 may thus be controlled via the MCU and initiated by the test button 104, by using the electrically connected PCBs. It will be appreciated by a person skilled in the art reading the present disclosure that the various PCBs may be connected together by e.g. flexible cable connections or any other suitable electrical connections.

The light source holder 206 comprises a lens portion (not shown) for directing light from the light source 106 at the gemstone under test. The lens portion may comprise a lens system, details of which are described in FIG. 5b below. The light source plunger 204 may protect the light sources e.g. 106 from dirt or other contaminants which may affect the wavelength and intensity precision of the light sources e.g. 106. The light source plunger/cover 204 may also be secured or fitted on to the light source holder 206, to enable the light source PCB 208 to be properly secure-fitted within the light source holder 206.

When assembled, the plurality of light sources e.g. 106 in the light source module 102 is arranged substantially directly above the aligned apertures 202a and 210 such that light from the plurality of light sources may be transmitted through the e.g. gemstone (under test) placed on the tray 202, through the apertures 202a and 210 and detected by the photo detector (e.g. numeral 404 of FIG. 4a) of the detector module (e.g. numeral 402 of FIG. 4a) within the main body 200.

The gemstone tester 100 may further comprise an energy module 212 for providing portable electrical power to the various electrical components and circuits formed on the various PCBs, including the PCBs (not shown) internal to the main body 200 and the light source PCB 208. In the example embodiment, the energy module 212 comprises a dry cell battery compartment 214 for allowing the stored electrical power in batteries to be harnessed. The provision of electrical power, to the various electrical components and circuits formed on the various PCBs, is controlled by the power button 112 as shown in FIG. 1b. When the energy module is providing power to the various electrical components and circuits formed on the various PCBs (i.e. the batteries are electrically connected), the power indicator 114 (FIG. 1b) is lit.

It will be appreciated that while the example embodiment shows dry cell batteries as a portable energy source, other energy sources may also be applicable.

The energy module 212 may further comprise a battery cover 216 which may be coupled to the dry cell battery compartment 214 to cover the batteries such that the batteries are enclosed within the energy module 212. This may prevent the batteries from being removed from the battery compartment or accidentally accessed when the gemstone tester 100 is in use. The cover 216 is removable such that the batteries may be replaced when necessary.

In the example embodiment, the gemstone tester 100 is a hand-held tool. That is, the gemstone tester 100 is preferably not constrained in operation by e.g. connection to a desktop processing machine or tool. In the example embodiment, the gemstone tester 100 is preferably used in a cableless configuration during operation. In the description, cableless is taken to include a connection that is without the use of wires or cables extending from the gemstone tester 100 to any other machine/tool. The gemstone tester 100 having the portable energy source may thus be portable to a user. By portable, it is meant, among other things, that the gemstone tester 100 is capable of being transported relatively easily. Preferably, the gemstone tester 100 may be carried in a pocket or palm-sized pouch. Therefore, the gemstone tester 100 can be more convenient over e.g. desktop setups for analysis.

FIG. 2 also shows the cover 120, which has been described in FIG. 1a, and is not further described here.

Figure 3A:
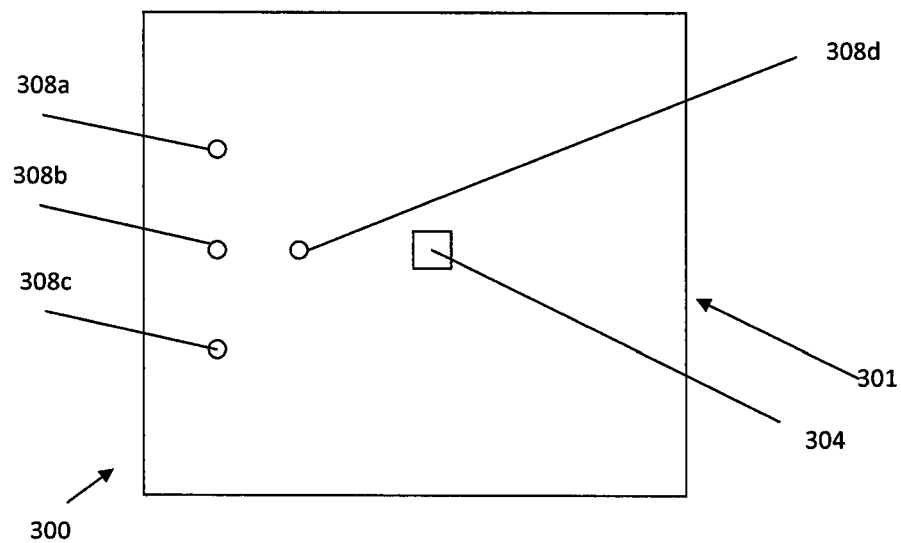
FIG. 3a shows a top view of a first PCB housed within the main body in an example embodiment.

FIG. 3a shows a top view of a first PCB 300 housed within the main body 200. The first PCB 300 is mounted against a top internal surface of the main body 200 (FIG. 2). The first PCB 300 comprises LEDs 308a-308d mounted on the top surface of the first PCB 300. The LEDs 308a-308d may function as a part of the indicators 108a-108d (FIGS. 1 and 2) respectively.

The first PCB 300 further comprises a test switch 304 which, when mechanically actuated, triggers the MCU (not shown) to begin a test, which comprises e.g. sequential switching/turning on and off of the light sources e.g. 106 (FIG. 2) and the operation of the light detector unit (not shown in FIG. 3). In this example embodiment, the test button 104 (FIG. 1) is mechanically coupled to the test switch 304 such that actuation of the test button 104 (FIG. 1) results in the actuation of the test switch 304. In this example embodiment, the MCU (not shown) may control the sequential switching on and off of the light sources e.g. 106 (FIG. 2) by controlling the supply power to the respective light sources.

Figure 3B:
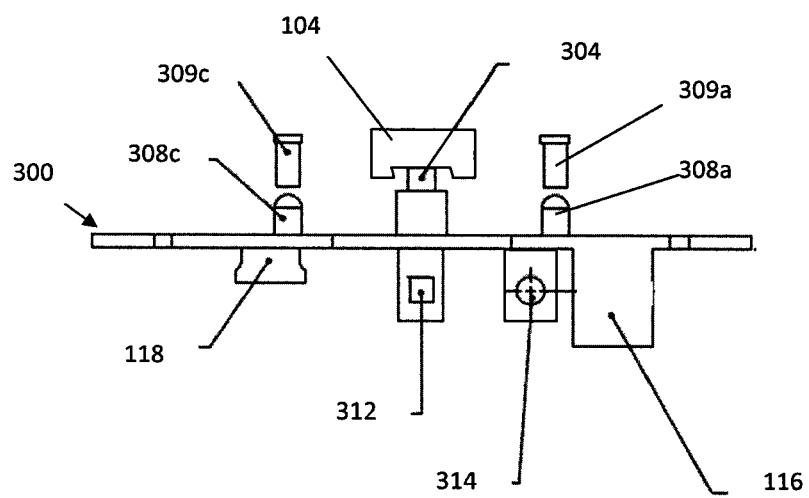
FIG. 3b shows a rear end view of the first PCB housed within the main body in an example embodiment.

FIG. 3b shows a rear end view of the first PCB 300 housed within the main body 200. The rear end view is a view of the rear end 301 of the PCB 300 (See FIG. 3a). The LEDs 308a and 308c are disposed on the first PCB 300 as shown. FIG. 3b further shows the presence of light pipes 309a and 309c disposed above the LEDs 308a and 308c. LEDs 308b and 308d are obscured by the test switch 304 in the current view. The light pipes 309a, 309c serve as respective wave guides to direct light out of the main body 200, such that the LEDs 308a and 308c may be more visible from outside (or external) the main body 200. Thus, the indicator 108a (FIGS. 1a and 2) comprises the LED 308a and light pipe 309a. Similarly, the indicators 108b-108d (FIGS. 1a and 2) comprises the respective LEDs 308b-308d and respective light pipes 309b-309d (partially shown).

The test switch 304 as described above in FIG. 3a is also shown in FIG. 3b. In addition, FIG. 3b further shows the test button 104 coupled to the test switch 304.

The first PCB 300 further comprises a power switch 312 mounted on an underside of the PCB 300. The power switch 312 is mechanically coupled to the power button 112 (FIG. 1b) located on the exterior of the gemstone tester 100 (FIG. 1b), in the same manner as the test switch 304 is coupled to the test button 104. When the power button 112 (FIG. 1b) is actuated, the power switch 312 is similarly actuated to power on or off the gemstone tester 100 (FIG. 1b).

The first PCB 300 further comprises another LED 314 mounted on the underside of the first PCB 300. As described above, the gemstone tester 100 is substantially a handheld device which may be powered by an internal energy source. Powering off the gemstone tester 100 (when not in use) may advantageously allow the energy source (e.g. energy module 212 of FIG. 2) to retain its energy capacity for a longer period. When the gemstone tester 100 is powered on, the LED 314 is lit to indicate the power status. The power indicator 114 (FIG. 1b) therefore comprises the LED 314, and may further comprise light pipes (not shown) which function similarly to e.g. the light pipe 309a for LED 308a.

The first PCB 300 further comprises the power jack 116, which allows an external power source to be connected to the gemstone tester 100 (FIG. 1b), and the data connector 118, which allows data to be transferred or communicated between the gemstone tester 100 (FIG. 1b) and an external processing device such as a computer (as shown in FIG. 1a). As described earlier, the data connector 118 is not limited to a USB (universal serial bus) connector as shown and may include, but is not limited to, e.g. Firewire, Ethernet, Thunderbolt, etc. The connector is also not limited to wired connections, and may include a wireless connection means.

Figure 4A:
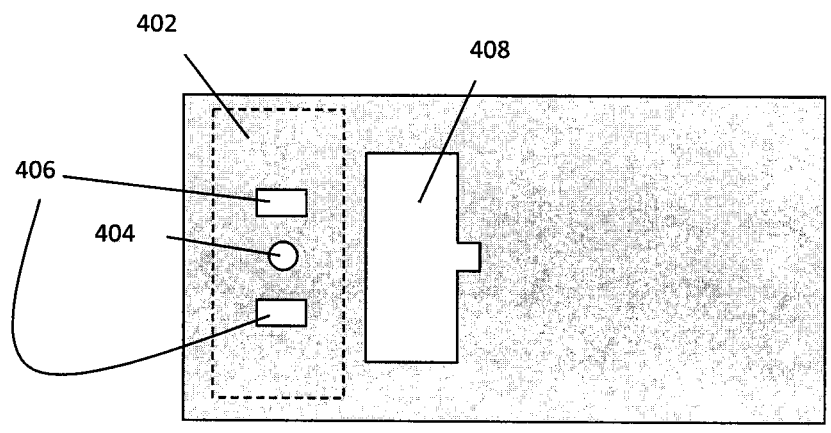
FIG. 4a shows a top view of a second PCB housed within the main body in an example embodiment.

FIG. 4a shows a top view of a second PCB 400 housed within the main body 200. The second PCB 400 is mounted against a bottom internal surface of the main body 200. The second PCB 400 comprises the detector module 402 (previously mentioned in FIGS. 1a and 2). The detector module 402 comprises a photo detector 404 and a potentiometer 406.

The second PCB 400 is mounted within the main body 200 (FIG. 2) such that the photo detector 404 is aligned with the aperture 210 (FIG. 2) of the main body 200 (FIG. 2). As described with reference to FIG. 2, during testing, the light from the light sources e.g. 106 (FIG. 2) may be transmitted through the e.g. gemstone (under test) placed on the tray 202, through the apertures 202a and 210 and may be detected by the photo detector 404 of the detector module 402 within the main body 200.

The potentiometer 406 functions to calibrate the photo detector 404, to e.g. provide a suitable calibration offset prior to the testing process. It will be appreciated by a person skilled in the art reading the disclosure that the potentiometer 406 may be a pre-amplifier.

The second PCB 400 further comprises a through-hole 408 which allows for the light source module 102 (FIG. 2) to be inserted through.

Figure 4B:
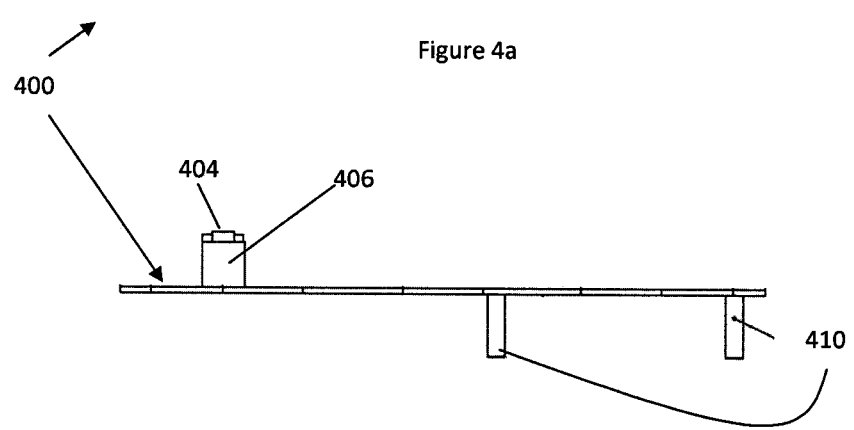
FIG. 4b shows a side view of the second PCB housed within the main body in an example embodiment.

FIG. 4b shows a side view of the second PCB 400 housed within the main body 200. As shown, the photo detector 404 and potentiometer 406 are mounted on a top surface of the second PCB 400. The second PCB 400 further comprises battery terminals 410 mounted on the underside of the second PCB 400. The battery terminals 410 are positioned such that they are aligned with connectors (not shown) of the battery compartment 214 (FIG. 2), such that batteries within the battery compartment 214 (FIG. 2) may be electrically connected to the second PCB 400. The alignment allows the batteries in the battery compartment 214 (FIG. 2) to power the electrical components when the power switch 304 (FIG. 3b) is turned on.

In the example embodiment, the photo detector 404 is a light sensor in the form of a photodiode capable of converting the light intensity detected into a voltage value. It will be appreciated that the photo detector 404 is not limited to a photodiode, and any kind of light sensor, which may provide or convert the light intensity detected into a voltage or analogue signal for use by other electrical components, may be used.

Figure 5A:
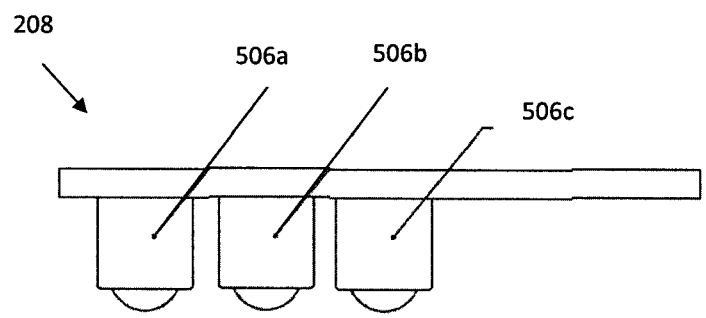
FIG. 5a shows a side view of a light source PCB in an example embodiment.

FIG. 5a shows a side view of the light source PCB 208 in an example embodiment. As described with reference to FIG. 2, the light source PCB 208 is housed within the light source module 102 (FIG. 2). The light source PCB 208 comprises a plurality of light sources in the form of LEDs 506a, 506b and 506c each capable of emitting light centered around (or of) a specific wavelength. The LEDs 506a, 506b and 506c are mounted on an underside of the light source PCB 208.

Figure 5B:
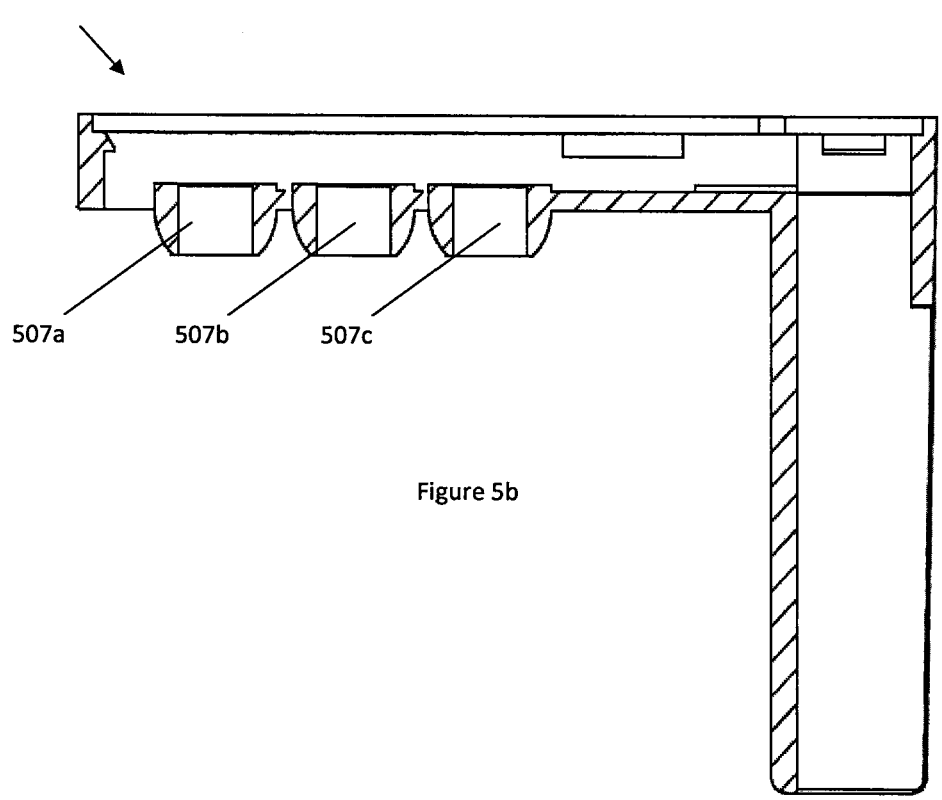
FIG. 5b shows a side view of a light source holder in an example embodiment.

FIG. 5b shows a side view of the light source holder 206 in the example embodiment. The light source holder 206 may comprise respective lens portions 507a-507c, each lens portions 507a-507c capable of receiving light from a respective one of the light sources (e.g. LEDs 506a-506c) and directing the received light to the photodetector or light detector 404 (FIG. 4). The lens portions 507a-507c may advantageously allow for more light to be received at the photodetector such that readings may be more accurate.

Figure 6:
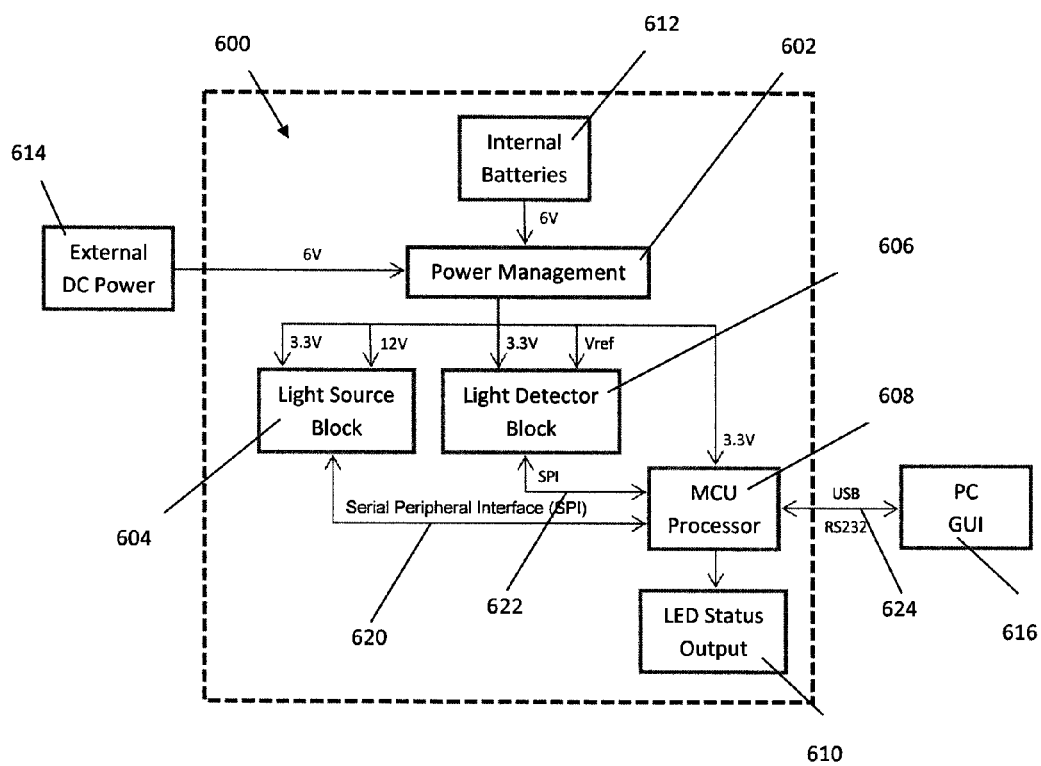
FIG. 6 shows a block diagram illustrating the electronic circuit components of a gemstone tester in an example embodiment.

FIG. 6 shows a block diagram illustrating the electronic circuit components of a gemstone tester 600 in an example embodiment. The gemstone tester 600 comprises a power management unit 602, a light source unit 604, a light detector unit 606, a microcontroller unit 608 and an output unit 610. It will be appreciated that each one of the components, e.g. the power management unit 602, the light source unit 604, the light detector unit 602, the microcontroller unit 608, and output unit 610 may be connected to any one of the PCBs 300, 400 or 208, as described with reference to FIGS. 3a, 3b, 4a, 4b and 5.

In the example embodiment, the gemstone tester 600 is powered by an internal power source 612 or an external power source 614, or a combination of the internal and external power sources 612 and 614. The power sources 612 and 614 are electrically connected or coupled to the power management unit 602, which in turn manages and provides a stable power accordingly to the light source unit 604, light detector unit 606 and microcontroller unit 608. That is, the power management unit 602 is electrically coupled to the light source unit 604, the light detector unit 606 and the microcontroller unit 608 respectively.

It will be appreciated that the internal power source 612 can be the batteries 216 as described with reference to FIG. 2. In addition, the second PCB 400 (FIG. 4) which comprises battery terminals 410 may provide the means for electrically connecting the batteries to the power management unit 602. As such, the power management unit 602 may be comprised in the second PCB 400 (FIG. 4). The connection to the external power source 612 may be provided by e.g. the power jack connector 116 (FIG. 1b) and may be provided on the first PCB 300, as described with reference to FIG. 1b and FIG. 3b. The light source unit 604 may be comprised within the light source PCB 208 as described with reference to FIG. 5a. The detector unit 606 may be comprised within the second PCB 400 as described with reference to FIG. 4b.

In the example embodiment, the power management unit 602 receives 6V DC (Direct Current) power supply from the internal power source 612 in the form of dry cell batteries. Alternatively, the power management unit 602 may receive 6V DC power from an external DC power source 614, such as an external battery. In a further alternative, the external power source may be a DC adaptor which adapts AC power supply into a stable and suitable DC power source for the power management unit 602.

It will be appreciated that the power management unit 602 may comprise electronic means for automatically switching to the external power source 614 when it is available, instead of drawing power from the internal power source 612. The internal DC power source 612 may also be in the form of rechargeable batteries which may be charged by the external DC power source 614 when connected.

In the example embodiment, the power management unit 602 provides a 3.3V and a 12V DC supply to the light source unit 604. The power management unit 602 also provides a 3.3V and a reference voltage, Vref, DC supply to the light detector unit 606. Vref is an operating voltage for an Analog-Digital-Convertor (ADC) component in the light detector unit 606. The power management unit 602 also provides a 3.3V DC supply to the microcontroller unit 608.

The microcontroller unit 608 and the light source block 604 communicate with each other in full duplex mode via a first SPI (Serial Peripheral Interface) bus connection or coupling 620. The microcontroller unit 608 and the light detector unit 606 communicate with each other in full duplex mode via a second SPI (Serial Peripheral Interface) bus connection or coupling. The microcontroller unit 608 also determines a status of the gemstone tester and drives the output unit 610 coupled to the microcontroller unit 608. In the example embodiment, the output unit 610 may comprise a plurality of indicators in the form of LEDs, for indicating a status or result of the gemstone tester. It will be appreciated that the plurality of indicators may be in the form of the indicators 108a-108d, as described with reference to FIG. 1a, and further described with reference to FIG. 3a. Thus, the output unit 610 may be comprised within the first PCB 300 (FIG. 3a). The microcontroller unit 608 may also be comprised within the first PCB 300 (FIG. 3a).

The microcontroller unit 608 is also provided with data communications interface connector(s) 624 to communicate with external devices such as a general purpose computer 616. The communication interface 624 may be e.g. a USB connector and/or a RS232 serial connector. The general purpose computer 616 may allow the microcontroller unit 608 to be programmed. Alternatively or additionally, the general purpose computer 616 may allow the data within the microcontroller unit 608 to be accessed. The data communications interface connector 624 may be in the form of the data connector 118 as described with reference to FIGS. 1a and 3b, and may be comprised within the first PCB 300 of FIGS. 3a and 3b.

Figure 7:
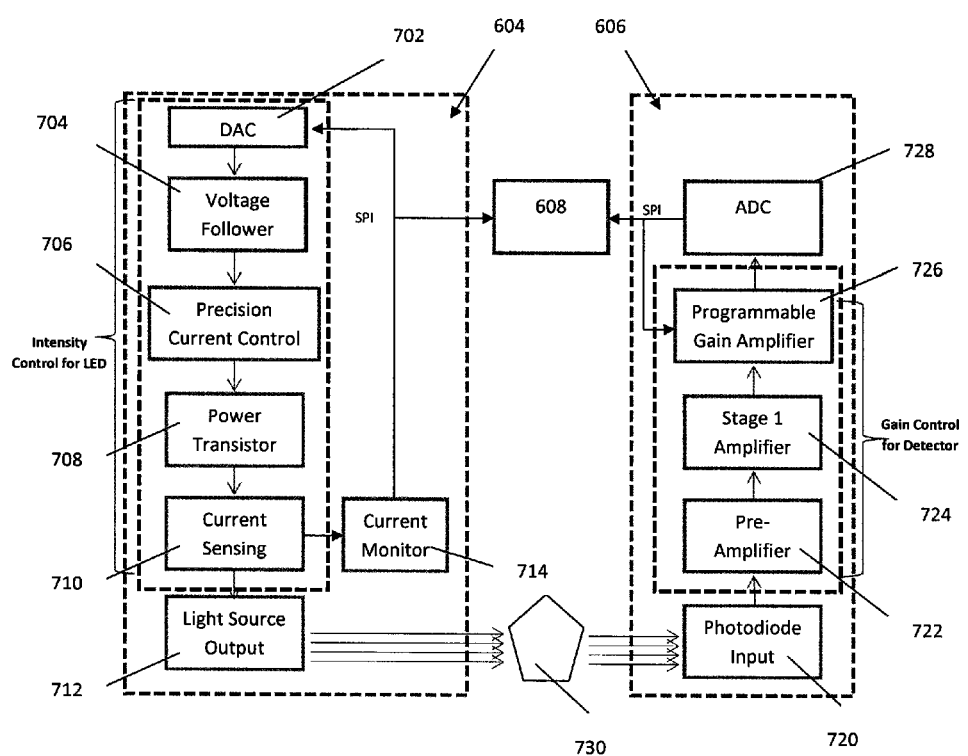
FIG. 7 shows a block diagram illustrating the electronic circuit components of a light source unit, a light detector unit and the interactions with a microcontroller unit in an example embodiment.

FIG. 7 shows a block diagram illustrating the electronic circuit components of the light source unit 604, the light detector unit 606 and the interactions with the microcontroller unit 608 in an example embodiment.

As described with reference to FIG. 6, electrical power is supplied from the power management unit 602 (FIG. 6) to each of the components within the light source unit 604, the light detector unit 606 and the microcontroller unit 608. The connections indicating the electrical power supply are not reproduced in FIG. 7 for clarity.

The light source unit 604 comprises a DAC (Digital-Analog-Converter) 702, a voltage follower 704 coupled to the DAC 702, a Precision Current Controller 706 coupled to the voltage follower 704, a Power Transistor 708 coupled to the Precision Current Controller 706, a Current Sensor 710 coupled to the Power Transistor 708, and a Light Source Output 712 coupled to the Current Sensor 710. In addition, the light source unit 604 may further comprise a Current Monitor 714 coupled to the Current Sensor 710.

The light detector unit 606 comprises a Photo Detector Input 720, a Pre-Amplifier 722 coupled to the Photo Detector Input 720, a First Stage Amplifier 724 coupled to the Pre-Amplifier 722, a Programmable Gain Amplifier 726 coupled to the First Stage Amplifier 724, and a ADC (Analog-Digital-Convertor) 728 coupled to the Programmable Gain Amplifier 726.

In operation, a gemstone 730 to be tested is placed between the light source output 712 and the light detector input 720. The microcontroller unit 608 provides a desired voltage level digitally to the DAC 702. The DAC 702 converts the desired voltage level to an analogue signal and outputs the analogue signal to a voltage follower 704. The voltage follower 704 buffers up the desired voltage level and sends it to the Precision Current Controller 706. The Precision Current Controller 706 converts the voltage to a current output to switch on the power transistor 708 such that current is provided to the Current Sensor 710, which passes on the current to the Light Source Output 712 such that the Light Source Output 712 is lit. The Current Sensor 710 also provides feedback to the Precision Current Controller 706 via the Voltage Follower 704 to ensure that the current output from the power transistor is of a relatively stable level. In so doing, the intensity of the light from the Light Source Output 712 is controlled. The Current Sensor 710 is also monitored by the Current Monitor 714 which converts a representative current output from the power transistor 708 to a suitable voltage output for use by the microcontroller unit 608. The microcontroller unit 608 may then determine if the current at the light source output 712 is at a desired value, and may accordingly adjust the input to the DAC 702.

Light produced at the Light Source Output 712 passes through the gemstone 730 under test and arrives at the light detector input 720. The light detector input 720 converts the received light intensity into an analogue voltage signal. The analogue voltage signal is cleaned of noisy signals by the Pre-Amplifier 722. That is, noise in the analogue voltage signal is removed by the Pre-Amplifier 722. Subsequently, the cleaned signal is provided to the First Stage Amplifier 724 for an initial/first amplification. Thereafter, the first amplified signal is further amplified by the Programmable Gain Amplifier 726 into a final analogue signal for use by the ADC 728. The ADC 728 converts the voltage level of the analogue signal into a digital signal and transmits the digital signal to the Microcontroller unit 608. Based on the digital signal, the Microcontroller unit 608 programs the further amplification to be applied at the Programmable Gain Amplifier 726. For example, if it is determined that the digital signal is too high which may indicate a saturation of the analogue signal and that a useful reading cannot be obtained, the amplification at the Programmable Gain Amplifier 726 may be reduced. Alternatively, if it is determined that the digital signal is too small, the amplification at the Programmable Gain Amplifier 726 may be increased. The amplitude of the digital signal may be compared against known threshold values to determine if the digital signal is too high or too low.

It will be appreciated by a person skilled in the art reading the disclosure that the light source output 712 may comprise a plurality of light sources. Each of the plurality of light sources in the light source output 712 emits a substantially narrow wavelength band of light centered about a specific wavelength. The MCU provides control switching means to electrically switch between the particular light source to be activated (or switched on) for the purposes of the testing or characterizing of the gemstone 730. In an alternative embodiment, the light source output may be a single light source of a broad wavelength range. The MCU may provide for the use of a series of optical filters to narrow the range of the broad band light source output to specific ranges such that a particular range of light is provided to the gemstone for testing. The MCU may also control switching between different optical filters such that different wavelengths of light may be emitted from the light source output 712. Thus, in some example embodiments, the MCU may provide for switching to be performed to switch the wavelength of light emitted from the light source output 712, such that the light detector input 720 can receive at least two transmittances, where each transmittance is a fraction of light of a specific wavelength that passes through the gemstone.

Figure 8:
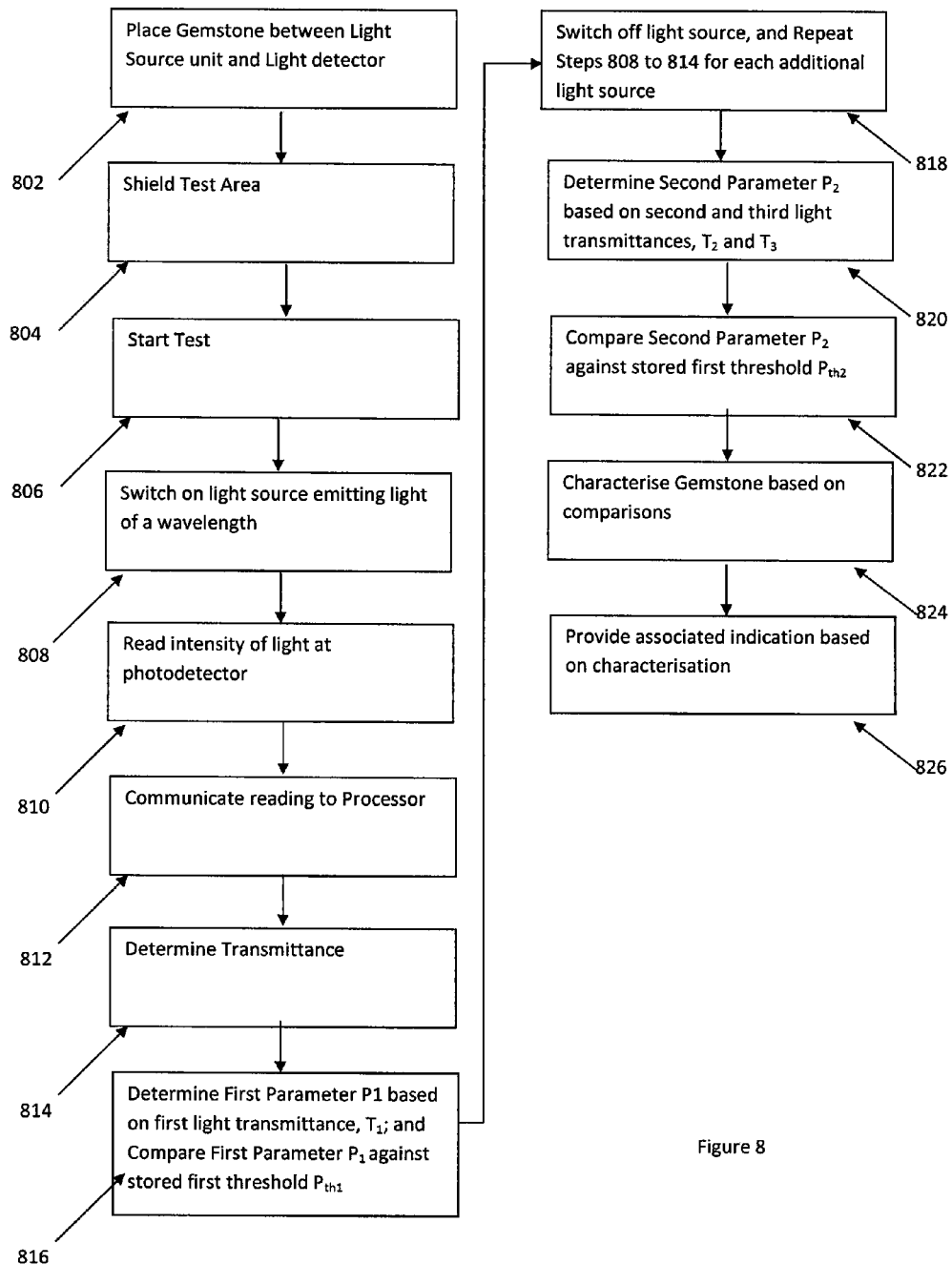
FIG. 8 shows a schematic flow chart illustrating a method for characterising a gemstone, in accordance with an example embodiment.

FIG. 8 shows a schematic flow chart 800 illustrating a method for characterizing a gemstone, in accordance with an example embodiment. At step 802, a gemstone is placed between a light source and a photo detector. In one example embodiment, the gemstone is placed on a tray (e.g. numeral 202 of FIG. 2) and moved onto a docking area for receiving the tray (e.g. numeral 202 of FIG. 2). Thereafter, at step 804, the cover (e.g. numeral 120 of FIG. 1) is attached to the main body of the gemstone tester (e.g. numeral 100 of FIG. 1) to shield the test area from ambient light. The test area includes the gemstone, the light sources (e.g. numeral 106 of FIG. 1) and the photodetector (e.g. numeral 404 of FIG. 4). At step 806, the start test button (e.g. numeral 104 of FIG. 1) is actuated. The start test button triggers a processor module in the form of an MCU (e.g. numeral 608 of FIG. 6) to begin the testing process.

At step 808, the MCU switches on a first light source (e.g. numeral 506*a* of FIG. 5*a*), such that a first wavelength of light is emitted from the light source module (e.g. numeral 102 of FIG. 1). The first wavelength may be about 250 nm to about 275 nm, or more preferably about 260 nm. It will be appreciated that other wavelengths may be used, for example, for determination of different gemstones. The light passes through the gemstone under test and the portion (or fraction) of the light that is transmitted/passes through the gemstone arrives at the photodetector (e.g. numeral 404 of the detector module 402 of FIG. 4). At step 810, the photo detector reads an intensity of light arriving at the photo detector and using the rest of the detector module (e.g. numeral 402 of FIG. 4) and communicates the reading to the MCU (at step 812). Based on the reading, the MCU determines a first light transmittance of the gemstone under test at step 814.

Thereafter, at step 816, a first parameter $P_1$ based on the first light transmittance $T_1$ is obtained. The parameter is obtained by applying a first formula to the first light transmittance. In the example embodiment, the parameter is obtained by a formula where the first light transmittance is used as-is. That is, the formula is $P_1=T_1$. Thereafter, the first parameter $P_1$ is compared against a stored threshold value $P_{th1}$. In the example embodiment, if the parameter value exceeds the threshold, i.e. $P_1 > P_{th1}$, the gemstone may be pre-classified as a synthetic gemstone. Otherwise, if the parameter value does not exceed the threshold, i.e. $P_1 \leq P_{th1}$, the gemstone may be pre-classified as a possible-natural gemstone accordingly. In alternative example embodiments, the gemstone may be pre-classified as a synthetic gemstone, if the parameter value does not exceed the threshold, i.e. $P_1 \leq P_{th1}$.

At step 818, the MCU switches or turns off the first light source and switches on a second light source (e.g. numeral 506*b* of FIG. 5*a*), such that a second wavelength of light is emitted from the light source module. The switching on of the second light source may be automatic. Alternatively, the switching on of the second light source may be based on the gemstone being pre-classified as a possible-natural gemstone. The second wavelength is different from the first wavelength. For example, the second wavelength may be about 330 nm. It will be appreciated that other wavelengths may be used, for example, for determination of different gemstones. The steps 808 to 814 are repeated such that a second light transmittance of the gemstone under test is determined.

Steps 808 to 814 are repeated as many times as desired to obtain as many light transmittances of the gemstone as desired. In the example embodiment, three light transmittances are determined. For example, a light source having a wavelength of about 475 nm may be used to obtain a third light transmittance. It will be appreciated that other wavelengths may be used, for example, for determination of different gemstones.

At step 820, a second parameter $P_2$ based on the second and third light transmittances $T_2$ and $T_3$ respectively is obtained. The parameter is obtained by applying a formula to the second and third light transmittances. In the example embodiment, the parameter is obtained by a formula where the ratio of the second and third light transmittances is obtained, i.e. the formula is $P_2=T_2/T_3$. Thereafter, at step 822, the second parameter $P_2$ is compared against a stored threshold value $P_{th2}$. In the example embodiment, if the parameter value exceeds the threshold, i.e. $P_2 > P_{th2}$ the gemstone may be pre-classified as a synthetic gemstone. Otherwise, if the parameter value does not exceed the threshold, i.e. $P_2 \leq P_{th2}$, the gemstone may be pre-classified as a natural gemstone accordingly. In alternative example embodiments, the gemstone may be pre-classified as a synthetic gemstone, if the parameter value does not exceed the threshold, i.e. $P_2 \leq P_{th2}$.

Finally, based on the comparisons in step 816 and step 822, it is determined whether the gemstone may be characterized as an e.g. natural gemstone, or synthetic gemstone at step 824. In the example embodiment, if any of first or second comparisons in steps 816 and 822 result in pre-classification of the gemstone as a synthetic gemstone, the gemstone may be classified as a synthetic gemstone. If both the first and second comparisons in steps 816 and 822 result in pre-classification of the gemstone as a natural gemstone, the gemstone may be classified as a potentially natural gemstone.

It has been recognised by the inventors that a user may classify a gemstone (such as a ruby) as a synthetic gemstone if the gemstone is classified as such at step 816. The test may be stopped at that step 816. On the other hand, if the gemstone is classified as a possible-natural gemstone at step 816, the user may proceed to steps 818 to 822 to use, for example, second and third light transmittances to classify the possible-natural gemstone as whether or not it is a synthetic gemstone at step 822.

At step 826, a characterization of a (potential) natural gemstone or synthetic gemstone results in specific status indicators being provided. For example, a characterization that a gemstone is (potentially) natural may result in a green LED being lit, while a characterization that a gemstone is synthetic may result in a red LED being lit. Alternatively, if the test is inconclusive, a yellow LED may be lit. In an illustrative example, for a two-step process to confirm a synthetic gemstone (e.g. a flux/hydrothermal type), the green LED may be lit first (e.g. under testing for the light transmittance at about 260 nm wavelength) to indicate that a gemstone under test is a possible-natural gemstone. This may e.g. eliminate that the gemstone under test is a flame-fusion synthetic gemstone. Thereafter, the red LED may be lit subsequently (e.g. under testing for the light transmittances at the wavelengths of about 330 nm and 475 nm) to confirm that the gemstone under test is a synthetic gemstone (e.g. made using a flux or hydrothermal process).

Experimental Results

The next section describes an experiment conducted to determine the use of two or more light sources of different wavelengths to facilitate the screening or characterization of gemstones. In particular, rubies were screened or characterized as synthetic rubies or natural rubies.

It will be appreciated that while the section discloses the characterization of rubies, the example embodiments of the present application are not limited to rubies only, and may further include other gemstones such as e.g. diamonds, emeralds, etc.

In the experiment, a total of 78 faceted ruby samples were obtained. The sample comprises 44 natural and 34 synthetic rubies. The natural rubies are of various origins such as Myanmar, Vietnam, Afghanistan, Pakistan, India, Thai-Cambodia and the east African region e.g. Tanzania, Kenya and Madagascar. The natural ruby set consists of a mixture of untreated and treated rubies of various treatment methods such as heat, heat with flux and heat with lead-glass fracture filling. The synthetic rubies are acquired from common production processes available in the market such as e.g. flame fusion process (Verneuil), flux grown process and hydrothermal process etc. There may be rubies manufactured by other processes. The quality of rubies used in this experiment ranges from transparent to translucent, and the colour of the rubies range from pinkish red to dark red which encompasses most colour varieties of rubies available in the market. The size of the rubies varies from about 0.1 to about 25 carats, and thus covers wide ranges of gemstones' sizes.

For each of the gemstones, a transmittance of non-polarised light of a spectrum range of 250 nm to 800 nm was obtained using a UV-Vis-NIR (Ultraviolet-Visible-Near Infrared) spectrophotometer. In the experiment, the spectrophotometer used is a Perkin Elmer Model: Lambda 950. The transmittance is the fraction of incident light that passes or is passed through the gemstone, at a particular wavelength.

All rubies used in the experiment were also subjected to chemical analysis (semi-quantitative method) for all major and minor chemical composition such as Alumina (Al), Titanium (Ti), Iron (Fe), Chromium (Cr), Vanadium (V) and Gallium (Ga), and are reported in the form of weight percentage of element oxide by using a EDXRF (Energy dispersive x-ray fluorescence) spectrometer. The data from the chemical analysis is compared with the transmission spectrum of each ruby to determine the relationship between each other.

Figure 9A:
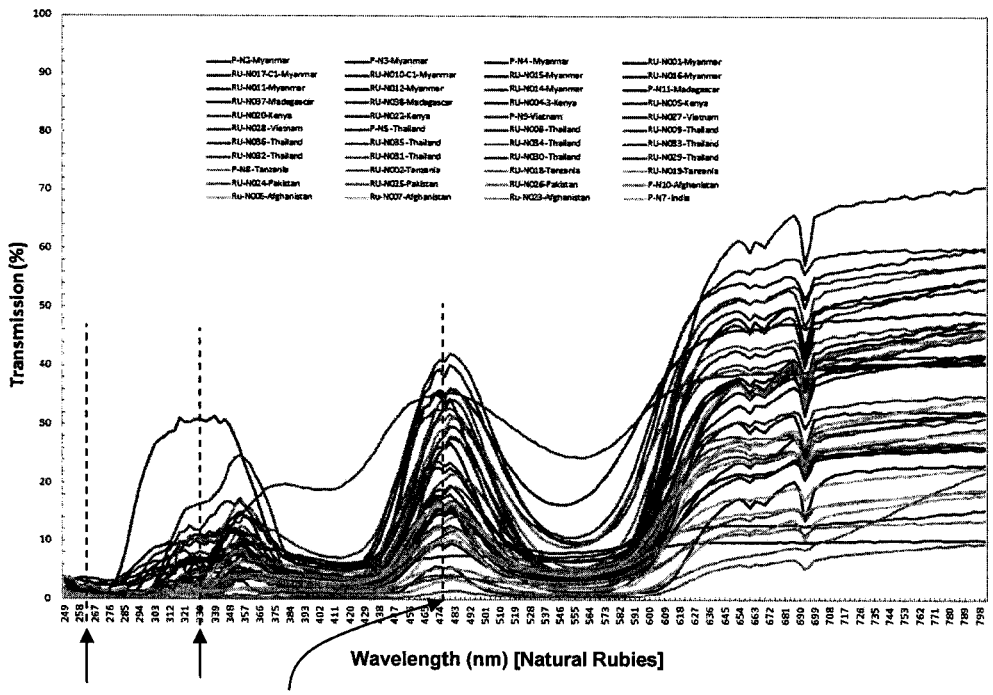
FIG. 9a shows transmission spectrums for natural rubies obtained using a spectrophotometer.
Figure 9B:
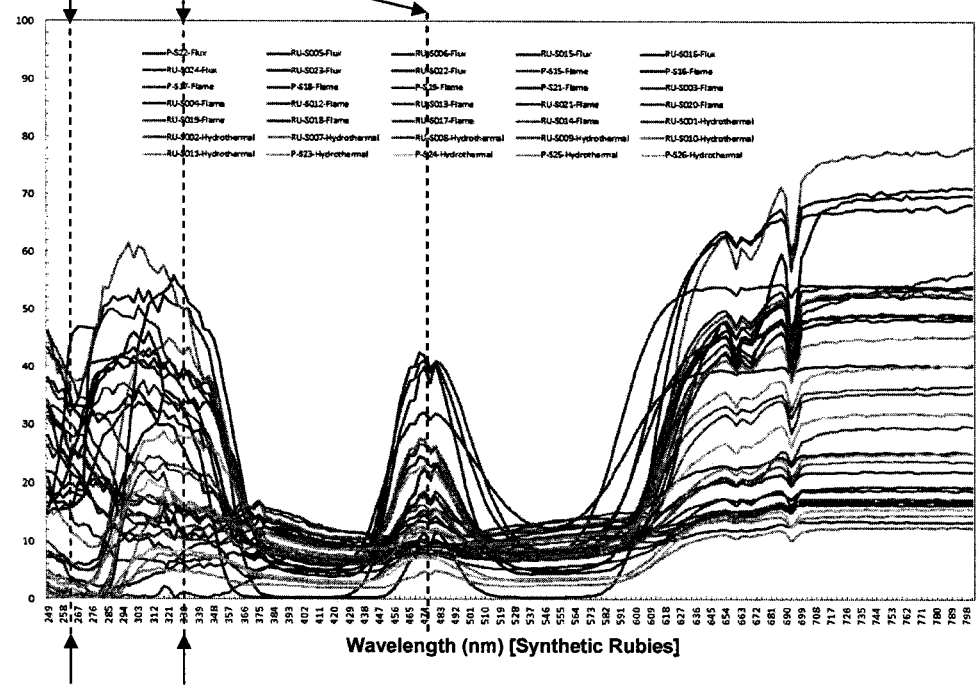
FIG. 9b shows transmission spectrums for synthetic rubies obtained using a spectrophotometer.

FIG. 9a shows the transmission spectrums for natural rubies obtained using the spectrophotometer. FIG. 9b shows the transmission spectrums for synthetic rubies obtained using the spectrophotometer.

As shown in FIG. 9a, all natural rubies in the sample show strong light absorption or poor light transmittance at the UV range (i.e. at the range from e.g. 250-275 nm), regardless of origin and treatment type. In contrast, as seen in FIG. 9b, the synthetic rubies show better light transmittance at the same UV range. Numeral 902 in FIGS. 9a and 9b show the light transmittance of natural and synthetic rubies respectively at the wavelength of about 260 nm.

The inventors have recognised that the difference in absorption/transmittance at the UV range may be due to the differences in structure and bonding between natural and synthetic gemstones. Synthetic gemstones may have a much higher degree of structural perfection than natural gemstones due to the nature of their growth processes, thereby resulting in better UV transmission. Thus, the inventors have recognised that the range of wavelengths from 250 to 275 nm may be utilized as fingerprint wavelengths to segregate between a possible-natural and a synthetic ruby. In other words, good transmittance at the UV range (e.g. 250 to 275 nm) may be an indication of a synthetic ruby, while poor transmittance at the UV range (e.g. 250 to 275 nm) may be an indication of a possible-natural ruby.

Based on the above findings, a light source in the form of an LED having a central wavelength of e.g. about 260 nm may be used in an example embodiment of the present application to characterise a gemstone as a either a synthetic or a possible-natural gemstone. It will be appreciated that 260 nm is an intermediate value between 250 nm to 275 nm.

Figure 10:
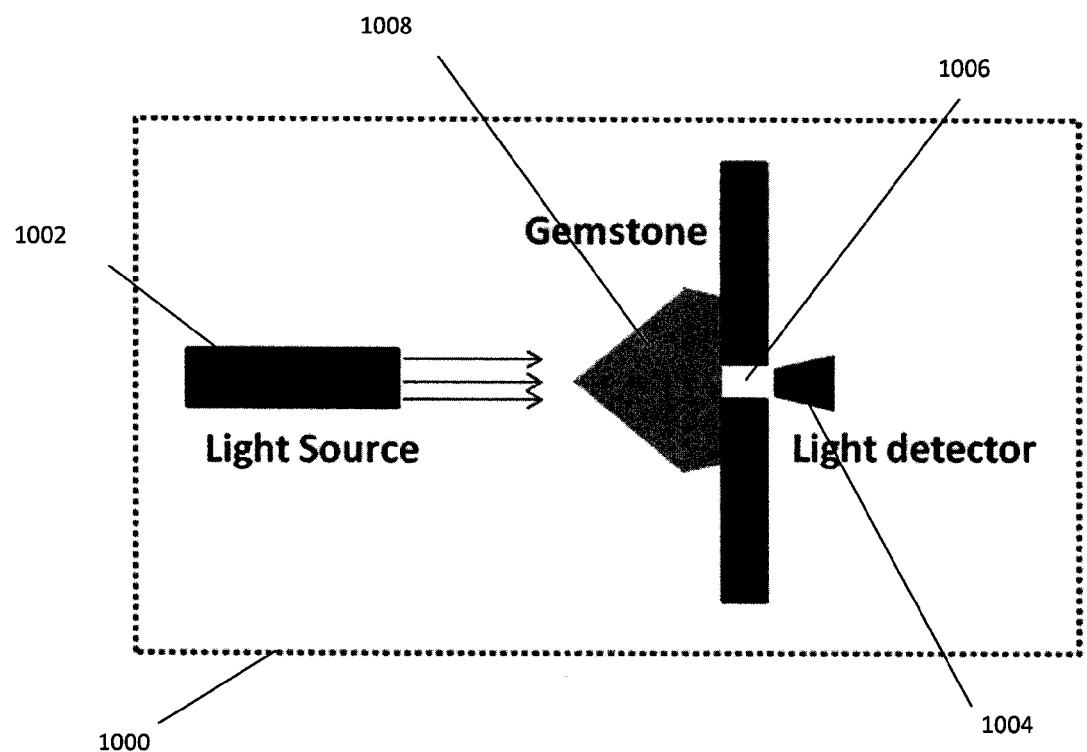
FIG. 10 shows a setup for measuring the optical transmission of rubies in an example embodiment.

A setup 1000 for measuring the optical transmission of rubies is illustrated in FIG. 10. The light source 1002 is a deep UV light emitting diode (LED) emitting a light of wavelength 260±5 nm. The usage of a deep UV LED offers several advantages over other traditional UV sources such as UV florescence lamps, gas discharge lamps (i.e. Deuterium lamp), etc. Deep UV LEDs may offer longer lifetimes, higher efficiencies, are smaller and more compact, when compared with the traditional UV sources. In addition, deep UV LEDs emit light of a smaller emission bandwidth (i.e., narrow spectral line width), without the need for an additional optical filter, when compared with other types of UV lamps which have a broader emission bandwidth. The photodetector 1004 employed in this setup 1000 is a schottky-type photodiode made using aluminium-gallium-nitride-based material which is capable of detecting spectral wavelength from 230 to 500 nm. In the setup 1000, the transmission window 1006 is about 2 mm wide in diameter. Thus, the gemstone 1008 under test measures greater than 2 mm wide.

Figures 11A, 11B:
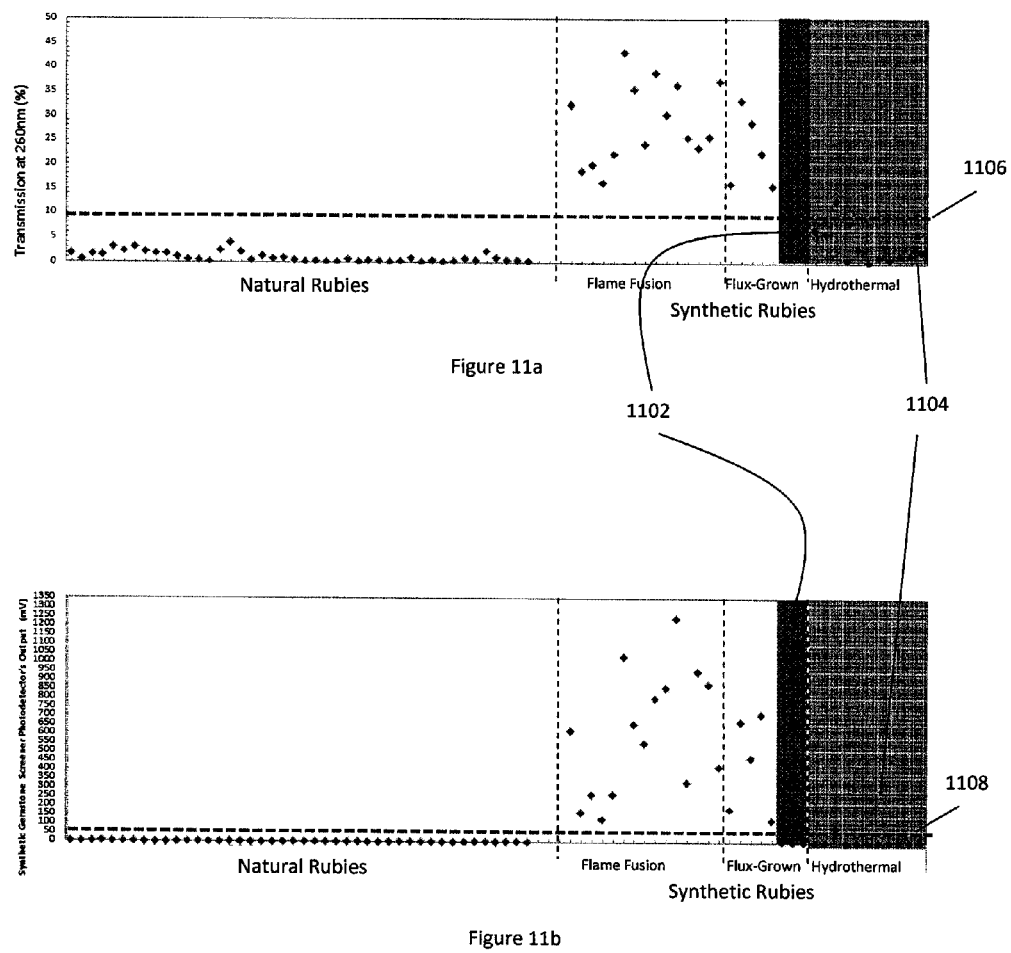
FIG. 11a shows the transmittance at about 260 nm of each of the sampled rubies using the spectrophotometer.
FIG. 11b shows the detected photodetector reading (in milli-volts) in an example embodiment.

FIG. 11a shows the transmittance at about 260 nm of each of the sampled rubies using the spectrophotometer. FIG. 11b shows the detected photodetector reading (in milli-volts) using the setup 1000 shown in FIG. 10. As shown in FIG. 11a, it is observed that a threshold cutoff of 10% UV (i.e., about 260 nm) transmittance may provide an indication that the ruby is not a natural (i.e. synthetic) ruby. That is, any gemstone with more than 10% transmittance at about 260 nm (or above line 1106), is determined not to be a natural ruby. Similarly, as shown in FIG. 11b, using the setup 1000 shown in FIG. 10, a photodetector 1004 reading beyond a threshold of more than about 50 mv (or above line 1108), indicates a synthetic ruby, and that the gemstone under test may be classified as a synthetic gemstone.

The inventors have recognised that the synthetic rubies with good transmittance at the UV wavelength range as seen from FIGS. 11a and 11b are rubies made from the flame fusion process. This is because of the almost 'pure' melt-growth process which introduces only relatively few elements to the gemstone during the synthesizing process. Thus, fewer defects arise in the crystal structures from such processes.

Thus, it is therefore possible to screen out rubies made from the flame fusion process, if transmittance at the wavelength range is lower than a certain threshold.

However, even with the elimination of rubies made from the flame fusion process, the inventors have recognised that there still exists a number of other types of synthetic rubies which cannot be discerned from natural rubies based on their UV transmittance at about 260 nm. As seen in FIGS. 11a and 11b, some synthetic rubies made from the flux growth process (represented at numeral 1102) and all synthetic rubies made from the hydrothermal process (represented at numeral 1104), have poor transmittance at the UV wavelength range (similarly to natural rubies).

The inventors have realised that the flux growth process is solution-based where a variety of chemical fluxes are used. This may in turn raise the likelihood of a defective crystal structure, causing poor transmittance at the UV wavelength range. This can be evidenced from the chemical analysis (i.e., EDXRF) of the common additive elements i.e., Ti, V, Ga, Fe (Titanium, Vanadium, Gallium and Iron respectively) in synthetic processes for synthetic rubies as shown in FIGS. 12a to 12d respectively.

As shown in FIGS. 12a-12d, the chemical analysis results show that the same few flux-grown rubies which exhibit poor transmittance at the UV wavelength range (represented at numeral 1102 in FIGS. 11a-11b) also show high concentrations of additive elements e.g., Ti, V and/or Ga (see numeral 1202 in the FIGS. 12a-12d). The inventors have recognised that this suggests a high possibility of crystal structure defects which is also consistent with the transmission measurements of the rubies obtained via the flux-growth process.

However, the inventors have also recognised that the poor UV transmittance of hydrothermal rubies (see numeral 1104 of FIGS. 11a-11b) is not related to the effects of high concentrations of additive elements. As shown in FIGS. 12a-12d, the hydrothermal rubies do not exhibit substantially higher Ti, V, Ga, and/or Fe contents compared with the other rubies. This may be attributed to the methods employed in the formation of hydrothermal synthetic rubies. Hydrothermal synthetic rubies are grown from a water-rich solution enclosed in a pressurized autoclave, thereby introducing a substantially large number of hydroxyl molecules to the crystal structures which may cause strong UV absorption at deep UV wavelengths, e.g., at about 260 nm.

Thus, the inventors have recognised that chemical analysis, in addition to UV transmittance, is not sufficient to distinguish hydrothermal rubies from natural rubies.

Returning to FIGS. 9a and 9b, the inventors recognised that the transmission intensities of the peaks at 330 nm (see numeral 904) and 475 nm (see numeral 906) display an inverse relationship for both synthetic and natural rubies, i.e., the transmission intensity at about 475 nm is greater than the peak transmission intensity at about 330 nm for natural rubies, and the reverse is true for synthetic rubies.

Figure 13:
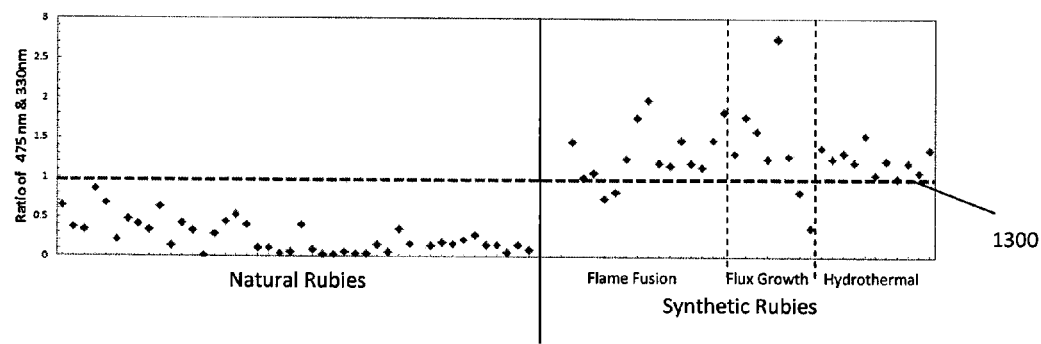
FIG. 13 shows a ratio of the transmittance at a wavelength of about 330 nm to the transmittance at a wavelength of about 475 nm, for each of the rubies in the sample in an example embodiment.

FIG. 13 shows a ratio of the transmittance at a wavelength of about 330 nm to the transmittance at a wavelength of about 475 nm, for each of the rubies in the sample. That is, for each of the rubies, the transmittance at about 330 nm is divided by the transmittance at about 475 nm wavelength. As shown in FIG. 13, for natural rubies, a ratio of the transmittance at about 330 nm wavelength to the transmittance at about 475 nm wavelength is less than 1. In contrast, it is observed that the synthetic rubies have ratios of transmittances of more than 1 (i.e. above the line 1300). Therefore, a gemstone may be classified as a natural gemstone, if the particular transmittance ratio is less than one. Otherwise, the gemstone may be classified as a synthetic gemstone, if the particular transmittance ratio is more than one.

Therefore, the inventors have recognised that it is feasible to use a transmittance at a wavelength of about 260 nm to exclude synthetic rubies and obtain a smaller sample of possible-natural rubies (i.e. comprising natural and some synthetic rubies). That is, any gemstone with more than 10% transmittance at about 260 nm wavelength is classified as a synthetic ruby. Next, from the smaller sample of possible-natural rubies, the inventors have recognised that it is feasible to use light transmittances at wavelengths of about 330 nm and about 475 nm to further obtain other synthetic rubies. That is, using a ratio of transmittances at about 330 nm wavelength to transmittances at about 475 nm wavelength, a ruby having a ratio that is more than a threshold value is classified as a synthetic ruby. In one example embodiment, a ruby is classified as a synthetic ruby if the ruby's ratio of transmittances at about 330 nm wavelength to transmittances at about 475 nm wavelength is more than one.

A gemstone tester was constructed to compare against current determination methods of whether a gemstone is synthetic or not. The gemstone tester was constructed for determination of rubies and is substantially similar to the device described in example embodiments. It is appreciated that the gemstone tester is not limited to determination of rubies and may be catered for determination of other gemstones such as diamonds etc.

The inventors found that the gemstone tester took about five to ten seconds to provide a determination of whether a ruby is a synthetic ruby. The gemstone tester compared advantageously in speed against the relatively long and tedious methods currently used for determination of whether a gemstone is synthetic or not. Current methods typically require a plurality of steps (e.g. three to ten steps) of testing a gemstone, and these may include conducting tests to determine elemental traces, fluorescence of the gemstone and optical microscopy analysis, etc. There are typically three to ten parameters that may need to be determined before a gemmologist begins to form a conclusion. In addition, current methods typically require a panel of gemmologists to use their collective experience to arrive at a conclusion on whether a gemstone is synthetic. It is known that in the event if the panel does not have a firm conclusion, other gemmologists may need to be involved or further tests may need to be carried out.

In addition, as compared to the various testing needed for current methods, it was relatively easy to place the ruby for using the light transmittances in the gemstone tester.

As such, the gemstone tester provided significant advantages over current determination methods.

Based on the above description, in one example embodiment of the present application, there is provided a gemstone tester for characterising gemstones as e.g. synthetic or natural gemstones.

In the example embodiment, the gemstone tester may comprise a detector unit capable for detecting one or more transmittances of the gemstone; and a processing unit for determining a first parameter based on one or more transmittances of light; and for characterising the gemstone based on the first parameter; wherein each transmittance of the gemstone is a fraction of light of a specific wavelength that is passed through the gemstone.

In the example embodiment, the gemstone tester may further comprise a light source unit for providing each specific wavelength of light. The light source unit may comprise a plurality of LEDs (Light Emitting Diodes), each LED providing or emitting each of the specific wavelengths of light. In the example embodiment, the light source unit comprises three LEDs, wherein the LEDs are capable of emitting light of wavelengths centered substantially about 260 nm, 330 nm and 475 nm respectively.

In an alternative example embodiment, the light source unit may comprise one light source and a plurality of optical filters. The one light source may be a broadband light source which emits light of a broader wavelength range. The optical filters may, either alone or in combination, filter the broadband light emitted from the light source such that only light of specific wavelengths are emitted from the light source unit. For example, the optical filters may filter a broadband light source which emits light of a wavelength of between 200 nm to 600 nm, such that light of wavelengths centered about 260 nm, 330 nm and 475 nm are allowed to be emitted by the optical filters.

In the example embodiment, the detector unit comprises a photo diode capable of providing a signal of a voltage level based on the intensity of light received. The voltage level is therefore representative of the transmittance of the gemstone of the particular wavelength of light. Hence, the detector unit may further comprise processing means to convert the voltage level provided by the photo diode to a transmittance value.

In the example embodiment, the light source unit further comprises a light source holder which can position the light source unit such that the detector unit is capable of detecting the transmittances of the gemstone. For example, in the example embodiment, the light source holder positions the light sources in the form of LEDs directly above the light detector unit. The light source holder may also further comprise directing means to direct the specific wavelengths of light at the detector unit. For example, it will be appreciated that the directing means may be in the form of a set of lens or focussing structure which can direct light at the detector unit. Alternatively, the directing means may further comprise mirrors or other reflective or refractive structures to direct light at the detector unit.

In the example embodiment, the processing unit of the gemstone tester may further comprise controller means for controlling the light source unit to provide the specific wavelengths of light in sequence, and said detector unit may detect the plurality of transmittances of the gemstone in sequence. For example, the light source unit may first emit light of about 260 nm for detection by the detector unit. Thereafter, the light source unit may then emit light of about 330 nm for detection by the detector unit. Subsequently, the light source unit emits light of about 475 nm for detection by the detector unit. It will be appreciated that the process of emitting light of the three wavelengths and its respective subsequent detection may be performed automatically by the processing unit. That is, once a test is initiated, further intervention on the gemstone tester by the user is not required. The processing unit may trigger the emission of light of the three wavelengths (e.g. 260 nm, 330 nm and 475 nm) from the light source unit in sequence, such that the respective light passes through the gemstone, and arrives at the light detector unit where transmittance of the gemstone for the three wavelengths of light (e.g. 260 nm, 330 nm and 475 nm) are determined. Alternatively, emission of light after the emission of the 260 nm wavelength light may be stopped if the gemstone is classified as a synthetic gemstone. Further emission of the e.g. 330 and 475 nm wavelengths light may be based on a user's command/actuation.

In an alternative embodiment, the process of emitting light of the three wavelengths and its respective subsequent detection may be based on a user's actuation for each wavelength of light. That is, the user triggers the emission of light of the first wavelength (e.g. 260 nm) such that the respective light passes through the gemstone, and arrives at the light detector unit where transmittance of the gemstone for the first wavelength of light (e.g. 260 nm) is determined. Thereafter, the user actuates a button to trigger the emission of the second wavelength of light (e.g. 330 nm), and subsequently, to also trigger the emission of the third wavelength of light (e.g. 475 nm).

In the example embodiment, the first parameter is determined by forming a relationship to one or more of the detected plurality of transmittances of light. The relationship may be through the application of a mathematical formula, which may involve one or more of a group consisting of a addition, subtraction, multiplication, or division, of a first transmittance of light. For example, in the example embodiment, the first parameter is determined by the gemstone's transmittance of light at the 260 nm wavelength (e.g. addition of zero).

In the example embodiment, the processing unit further comprises a storage memory for storing one or more threshold values; wherein the gemstone may be characterised based on the first parameter in comparison with one of the threshold values. For example, in the example embodiment, the first parameter (which is the gemstone's transmittance of light at the 260 nm wavelength) is compared with a first threshold value of 50 mv (millivolts). If the first parameter exceeds the first threshold value of "50 mv", the gemstone is characterised as a synthetic gemstone. Otherwise, if the first parameter does not exceed the first threshold value of "50 mv", the gemstone is characterised as a (potentially) genuine, or possible-natural, gemstone.

In the example embodiment, the processing unit further determines a second parameter based on two or more of the plurality of transmittances of light; and characterises the gemstone based on the first and second parameters. The second parameter is determined by forming an other relationship to two or more of the detected plurality of transmittances of light. For example, in the example embodiment, when characterising the gemstone, in addition to the above mentioned first parameter (where the gemstone's transmittance of light at 260 nm wavelength is considered), a second parameter is also considered, which takes into account the gemstone's transmittances of light at the 330 nm and 475 nm wavelengths.

In the example embodiment, the second parameter is determined by forming a relationship between two or more of the detected plurality of transmittances of light. The relationship may be through the application of a mathematical formula, which may involve one or more of a group consisting of a ratio, addition, subtraction, multiplication, or division, between a second and a third transmittance of light. For example, in the example embodiment, the second parameter is determined by obtaining a ratio of the gemstone's transmittance of light at the 330 nm wavelength to the gemstone's transmittance of light at the 475 nm wavelength.

In the example embodiment, the storage memory also stores another threshold value; wherein the gemstone is characterised based on the first and second parameters in comparison with respective first and second threshold values.

For example, in the example embodiment, the second parameter (which is the ratio of the gemstone's transmittance of light at the 330 nm wavelength to the gemstone's transmittance of light at the 475 nm wavelength) is compared with the threshold value of "1". If the first parameter exceeds the threshold value of "1", the gemstone is characterised as a synthetic gemstone. Otherwise, if the first parameter does not exceed the threshold value of "1", the gemstone is characterised as a (potentially) genuine gemstone.

In the example embodiment, a two-step process is disclosed for the classification of a gemstone. In the first step, a first parameter which takes into consideration the gemstone's transmittance of light at a first, for example about 260 nm, wavelength is determined and compared against a first threshold. In particular, a gemstone is classified as a synthetic gemstone if the first parameter exceeds the first threshold. In the second step, e.g. performed for a gemstone classified as a possible-natural gemstone in the first step, a second parameter which takes into consideration the gemstone's transmittances of light at different wavelengths, for example at about 330 nm and about 475 nm wavelengths, is determined and compared against a second threshold. In particular, a gemstone is classified as a synthetic gemstone if the second parameter exceeds the second threshold. It will be appreciated that the process may be stopped at the first step if the gemstone is classified as a synthetic gemstone.

In the example embodiment, the gemstone tester further comprises one or more indicators for indicating a status of the tester, based on the characterisation of the gemstone.

In the example embodiment, the gemstone tester further comprises a power unit for providing portable electrical power to the gemstone tester.

In the example embodiment, the gemstone the gemstone is one of a group consisting of rubies, diamonds, sapphires, and emeralds.

Example embodiments of the present application may provide a gemstone tester which, in utilizing a plurality of gemstone transmittances, may obtain a more accurate classification of gemstones. Compared to a gemstone tester in which only a single transmittance is utilized for the characterisation of the gemstone, example embodiments of the present application may enhance the accuracy of the gemstone characterisation.

Example embodiments of the present application may also provide a gemstone classification system which is portable and hand held, which may facilitate ease of use for a user. In contrast with the bulky equipment e.g. desk-bound and/or room sized, example embodiments of the present application may advantageously allow for quick and easy characterisation of the gemstone at any location.

The example embodiments of the present application may be applicable to the testing or characterization of gemstones which may include, but is not limited to, rubies, diamonds, sapphires, and emeralds etc. While some of the example embodiments described herein relate directly to the characterisation of rubies, it will be appreciated that the example embodiments may be modified to characterise e.g. diamonds, sapphires, emeralds etc. by e.g. changing the light source(s) and/or photo detector accordingly. For example, to characterise e.g. diamonds, a relationship between a first and second transmittance of light may be addition, subtraction, division and/or multiplication. The relationship may be compared against a threshold value. In addition or as an alternative, to characterise e.g. diamonds, a transmittance of light may be compared directly to a threshold value.

Further to the above, in described example embodiments, the detector unit or photo detector or photodiode are not limited as such. For example, a plurality of detectors may be implemented. Such detectors may be dedicated to detection within a narrow waveband. For example, to detect a transmittance at a wavelength of about 260 nm, a photodiode that can detect transmittances in a narrow waveband of between 260 nm to 275 nm may be utilised. A different photodiode may be utilised for transmittance at a different wavelength e.g. at about 330 nm.

In addition, in some example embodiments implementing the method of example embodiments, the detector unit may be a spectrometer. Transmittance values read by the detector unit may be provided to a separate processing unit for further processing e.g. to compare against one or more thresholds and/or to form a relationship between different transmittances etc., for determination of whether a gemstone is a synthetic gemstone.

Figure 16:
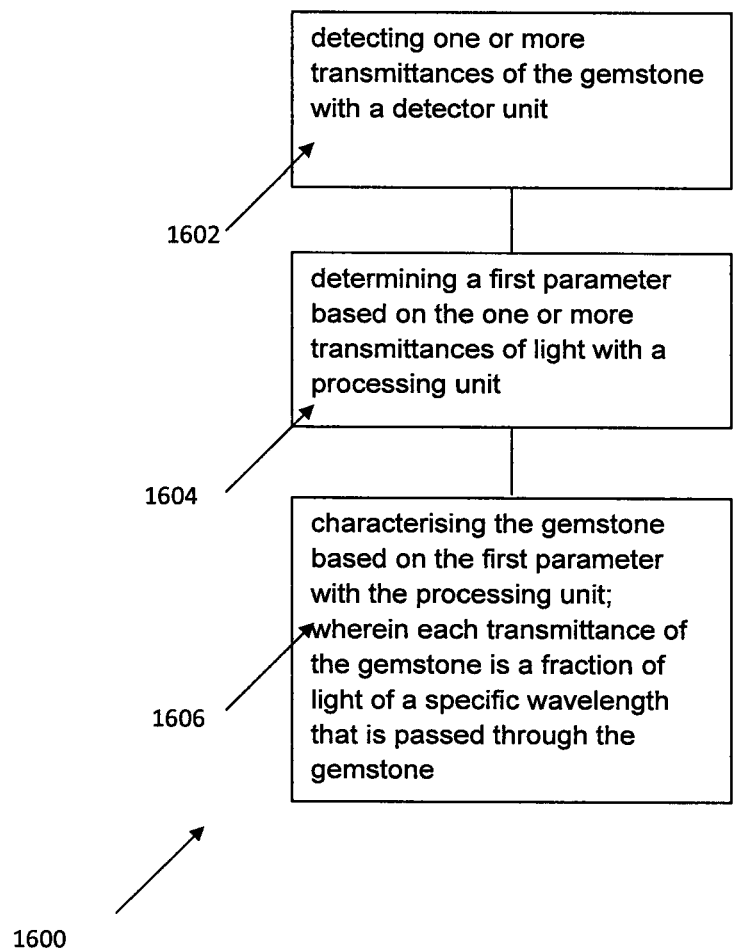
FIG. 16 shows a method of characterising a gemstone in an example embodiment.

FIG. 16 shows a method 1600 of characterising a gemstone in an example embodiment. At step 1602, one or more transmittances of the gemstone is detected with a detector unit. At step 1604, a first parameter is determined based on the one or more transmittances of light with a processing unit. At step 1606, the gemstone is characterised based on the first parameter with the processing unit, wherein each transmittance of the gemstone is a fraction of light of a specific wavelength that is passed through the gemstone.

Figure 14:
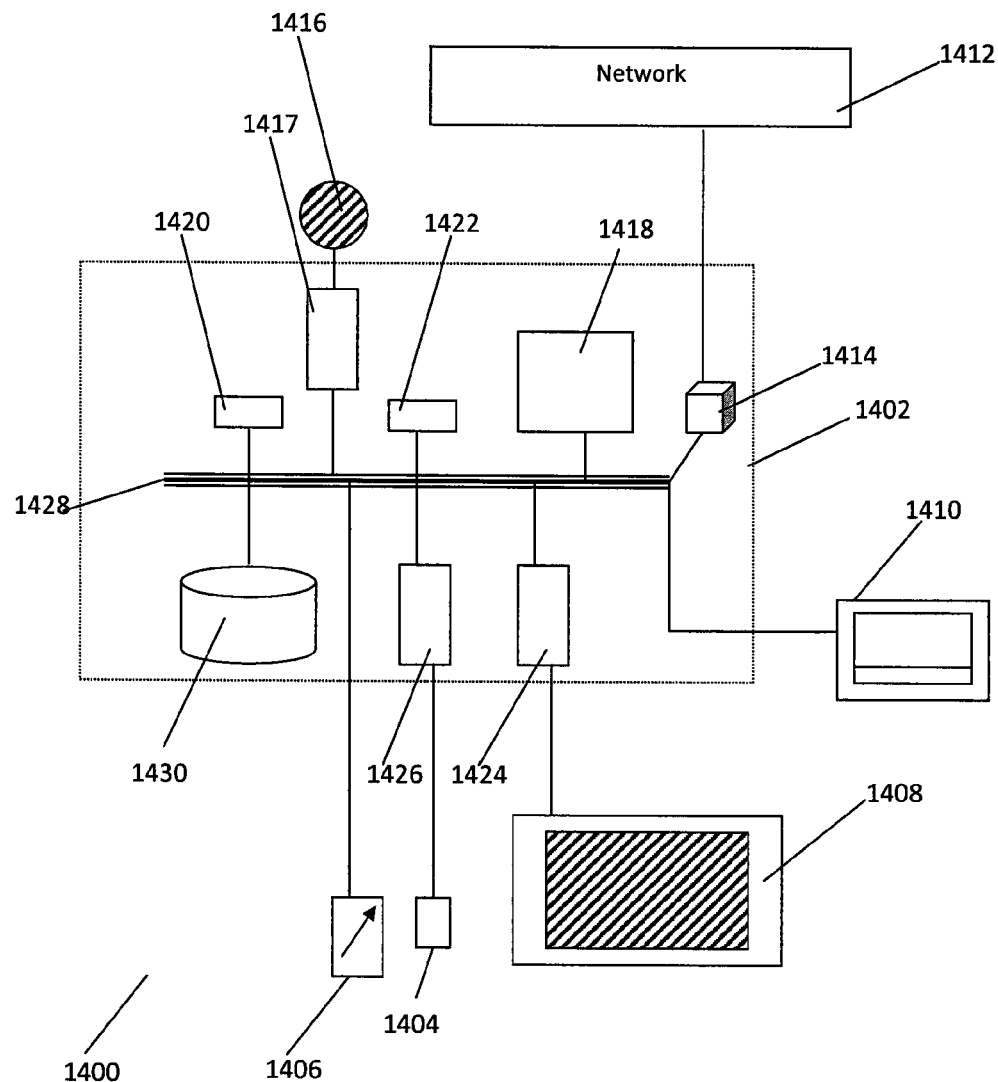
FIG. 14 is a schematic drawing of a computer system suitable for implementing an example embodiment.

Different example embodiments can be implemented in the context of data structure, program modules, program and computer instructions executed in a computer implemented environment. A general purpose computing environment is briefly disclosed herein. One or more example embodiments may be embodied in one or more computer systems, such as is schematically illustrated in FIG. 14. For example, the process of determining parameters and characterising gemstones may be performed by a computer system. Instructions to switch on or off light sources may also be sent by a computer system.

One or more example embodiments may be implemented as software, such as a computer program being executed within a computer system 1400, and instructing the computer system 1400 to conduct a method of an example embodiment.

The computer system 1400 comprises a computer module 1402, input modules such as a keyboard 1404 and a pointing device 1406 and a plurality of output devices such as a display 1408, and printer 1410. A user can interact with the computer module 1402 using the above devices. The pointing device can be implemented with a mouse, track ball, pen device or any similar device. One or more other input devices (not shown) such as a joystick, game pad, satellite dish, scanner, touch sensitive screen or the like can also be connected to the computer module 1402. The display 1408 may include a cathode ray tube (CRT), liquid crystal display (LCD), field emission display (FED), plasma display or any other device that produces an image that is viewable by the user.

The computer module 1402 can be connected to a computer network 1412 via a suitable transceiver device 1414, to enable access to e.g. the Internet or other network systems such as Local Area Network (LAN) or Wide Area Network (WAN) or a personal network. The network 1412 can comprise a server, a router, a network personal computer, a peer device or other common network node, a wireless telephone or wireless personal digital assistant. Networking environments may be found in offices, enterprise-wide computer networks and home computer systems etc. The transceiver device 1414 can be a modem/router module located within or external to the computer module 1402, and may be any type of modem/router such as a cable modem or a satellite modem.

It will be appreciated that network connections shown are exemplary and other ways of establishing a communications link between computers can be used. The existence of any of various protocols, such as TCP/IP, Frame Button, Ethernet, FTP, HTTP and the like, is presumed, and the computer module 1402 can be operated in a client-server configuration to permit a user to retrieve web pages from a web-based server. Furthermore, any of various web browsers can be used to display and manipulate data on web pages.

The computer module 1402 in the example comprises a processor 1418, a Random Access Memory (RAM) 1420 and a Read Only Memory (ROM) 1422. The ROM 1422 can be a system memory storing basic input/output system (BIOS) information. The RAM 1420 can store one or more program modules such as operating systems, application programs and program data.

The computer module 1402 further comprises a number of Input/Output (I/O) interface modules, for example I/O interface module 1424 to the display 1408, and I/O interface module 1426 to the keyboard 1404. The components of the computer module 1402 typically communicate and interface/couple connectedly via an interconnected system bus 1428 and in a manner known to the person skilled in the relevant art. The bus 1428 can be any of several types of bus structures including a memory bus or memory controller, a peripheral bus, and a local bus using any of a variety of bus architectures.

It will be appreciated that other devices can also be connected to the system bus 1428. For example, a universal serial bus (USB) interface can be used for coupling a video or digital camera to the system bus 1428. For example, a gemstone tester may be coupled to the bus 1428 for transmitting and receiving data to the tester. Data such as detected transmittances may be received at the computer module 1402. An IEEE 1394 interface may be used to couple additional devices to the computer module 1402. Other manufacturer interfaces are also possible such as FireWire developed by Apple Computer and i.Link developed by Sony. Coupling of devices to the system bus 1428 can also be via a parallel port, a game port, a PCI board or any other interface used to couple an input device to a computer. It will also be appreciated that, while the components are not shown in the figure, sound/audio can be recorded and reproduced with a microphone and a speaker. A sound card may be used to couple a microphone and a speaker to the system bus 1428. It will be appreciated that several peripheral devices can be coupled to the system bus 1428 via alternative interfaces simultaneously.

An application program can be supplied to the user of the computer system 1400 being encoded/stored on a data storage medium such as a CD-ROM or flash memory carrier. The application program can be read using a corresponding data storage medium drive of a data storage device 1430. The data storage medium is not limited to being portable and can include instances of being embedded in the computer module 1402. The data storage device 1430 can comprise a hard disk interface module and/or a removable memory interface module (both not shown in detail) respectively coupling a hard disk drive and/or a removable memory drive to the system bus 1428. This can enable reading/writing of data. Examples of removable memory drives include magnetic disk drives and optical disk drives. The drives and their associated computer-readable media, such as a floppy disk provide nonvolatile storage of computer readable instructions, data structures, program modules and other data for the computer module 1402. It will be appreciated that the computer module 1402 may include several of such drives. Furthermore, the computer module 1402 may include drives for interfacing with other types of computer readable media.

The application program is read and controlled in its execution by the processor 1418. Intermediate storage of program data may be accomplished using RAM 1420. The method(s) of the example embodiments can be implemented as computer readable instructions, computer executable components, or software modules. One or more software modules may alternatively be used. These can include an executable program, a data link library, a configuration file, a database, a graphical image, a binary data file, a text data file, an object file, a source code file, or the like. When one or more computer processors execute one or more of the software modules, the software modules interact to cause one or more computer systems to perform according to the teachings herein.

The operation of the computer module 1402 can be controlled by a variety of different program modules. Examples of program modules are routines, programs, objects, components, data structures, libraries, etc. that perform particular tasks or implement particular abstract data types. The example embodiments may also be practiced with other computer system configurations, including handheld devices, multiprocessor systems, microprocessor-based or programmable consumer electronics, network PCs, minicomputers, mainframe computers, personal digital assistants, mobile telephones and the like. Furthermore, the example embodiments may also be practiced in distributed computing environments where tasks are performed by remote processing devices that are linked through a wireless or wired communications network. In a distributed computing environment, program modules may be located in both local and remote memory storage devices.

Figure 15:
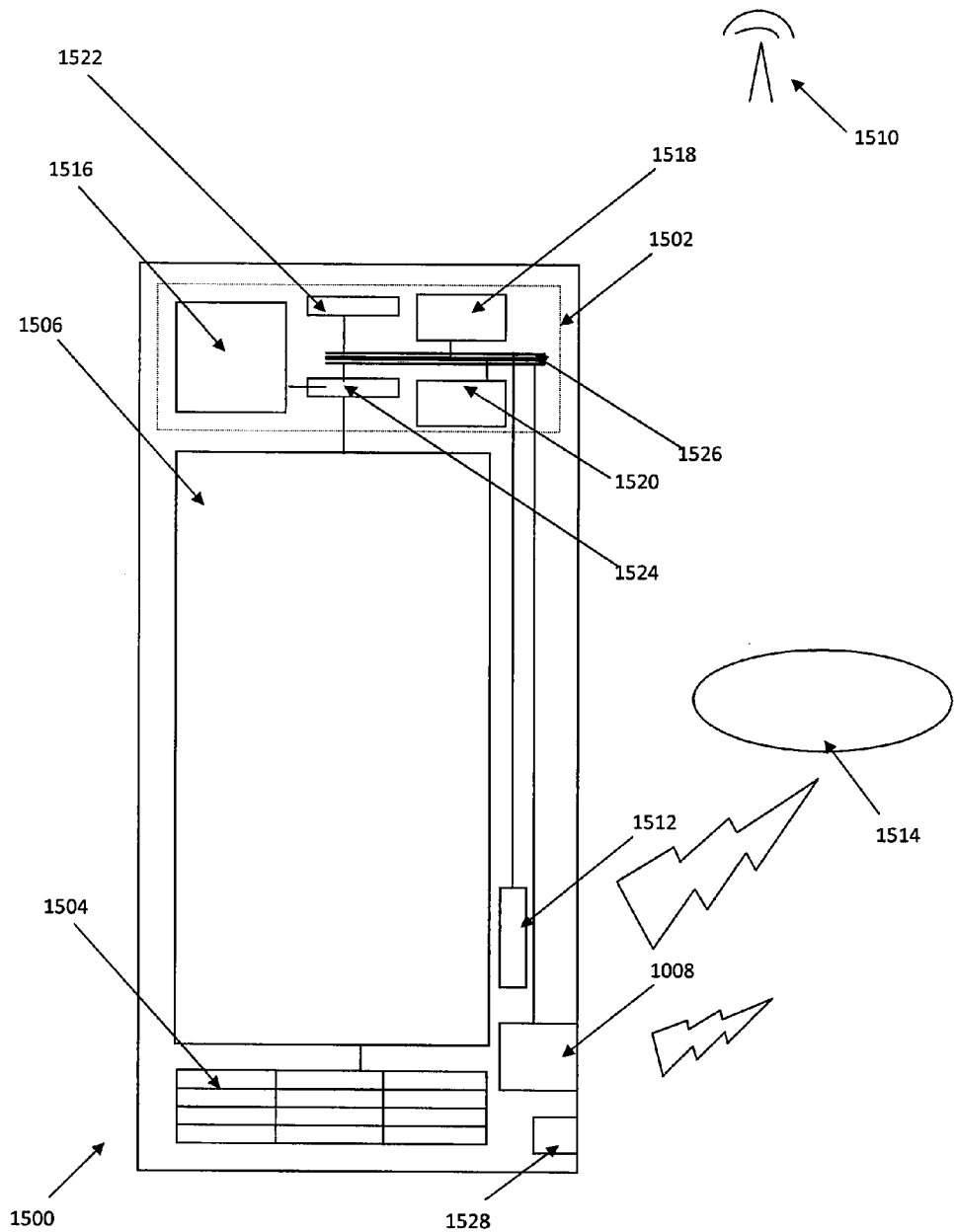
FIG. 15 is a schematic drawing of a wireless communication device suitable for implementing an example embodiment.

Different example embodiments may also be implemented in the context of data structure, program modules, program and computer instructions executed in a communication device. For example, the gemstone tester may be in the form of a wireless communication device. An exemplary communication device is briefly disclosed herein. One or more example embodiments may be embodied in one or more communication devices e.g. 1500, such as is schematically illustrated in FIG. 15.

One or more example embodiments may be implemented as software, such as a computer program being executed within a communication device 1500, and instructing the communication device 1500 to conduct a method of an example embodiment.

The communication device 1500 comprises a processor module 1502, an input module such as a touchscreen interface or a keypad 1504 and an output module such as a display 1506 on a touchscreen.

The processor module 1502 is coupled to a first communication module 1508 for communication with a cellular network 1510. The first communication module 1508 can include, but is not limited to, a subscriber identity module (SIM) card loading bay. The cellular network 1510 can, for example, be a 3G or 4G network.

The processor module 1502 is further coupled to a second communication module 1512 for connection to a network 1514. For example, the second communication module 1512 can enable access to e.g. the Internet or other network systems such as Local Area Network (LAN) or Wide Area Network (WAN) or a personal network. The network 1514 can comprise a server, a router, a network personal computer, a peer device or other common network node, a wireless telephone or wireless personal digital assistant. Networking environments may be found in offices, enterprise-wide computer networks and home computer systems etc. The second communication module 1512 can include, but is not limited to, a wireless network card or an eternet network cable port. The second communication module 1512 can also be a modem/router module and may be any type of modem/router such as a cable-type modem or a satellite-type modem.

It will be appreciated that network connections shown are exemplary and other ways of establishing a communications link between computers can be used. The existence of any of various protocols, such as TCP/IP, Frame Button, Ethernet, FTP, HTTP and the like, is presumed, and the communication device 1500 can be operated in a client-server configuration to permit a user to retrieve web pages from a web-based server. Furthermore, any of various web browsers can be used to display and manipulate data on web pages.

The processor module 1502 in the example includes a processor 1516, a Random Access Memory (RAM) 1518 and a Read Only Memory (ROM) 1520. The ROM 1520 can be a system memory storing basic input/output system (BIOS) information. The RAM 1518 can store one or more program modules such as operating systems, application programs and program data.

The processor module 1502 also includes a number of Input/Output (I/O) interfaces, for example I/O interface 1522 to the display 1506, and I/O interface 1524 to the keypad 1504.

The components of the processor module 1502 typically communicate and interface/couple connectedly via an interconnected bus 1526 and in a manner known to the person skilled in the relevant art. The bus 1526 can be any of several types of bus structures including a memory bus or memory controller, a peripheral bus, and a local bus using any of a variety of bus architectures.

The processor module 1502 may perform the functions of e.g. the processing of determining parameters and characterising gemstones, and instructions to switch on/off light sources etc.

It will be appreciated that other devices can also be connected to the system bus 1526. For example, a universal serial bus (USB) interface can be used for coupling an accessory of the communication device, such as a card reader, to the system bus 1526.

The application program is typically supplied to the user of the communication device 1500 encoded on a data storage medium such as a flash memory module or memory card/stick and read utilising a corresponding memory reader-writer of a data storage device 1528. The data storage medium is not limited to being portable and can include instances of being embedded in the communication device 1500.

The application program is read and controlled in its execution by the processor 1516. Intermediate storage of program data may be accomplished using RAM 1518. The method(s) of the example embodiments can be implemented as computer readable instructions, computer executable components, or software modules. One or more software modules may alternatively be used. These can include an executable program, a data link library, a configuration file, a database, a graphical image, a binary data file, a text data file, an object file, a source code file, or the like. When one or more processor modules execute one or more of the software modules, the software modules interact to cause one or more processor modules to perform according to the teachings herein.

The operation of the communication device 1500 can be controlled by a variety of different program modules. Examples of program modules are routines, programs, objects, components, data structures, libraries, etc. that perform particular tasks or implement particular abstract data types.

The example embodiments may also be practiced with other computer system configurations, including handheld devices, multiprocessor systems/servers, microprocessor-based or programmable consumer electronics, network PCs, minicomputers, mainframe computers, personal digital assistants, mobile telephones and the like. Furthermore, the example embodiments may also be practiced in distributed computing environments where tasks are performed by remote processing devices that are linked through a wireless or wired communications network. In a distributed computing environment, program modules may be located in both local and remote memory storage devices.

It will be appreciated by a person skilled in the art that other variations and/or modifications may be made to the specific embodiments without departing from the scope of the invention as broadly described. The present embodiments are, therefore, to be considered in all respects to be illustrative and not restrictive.

The invention claimed is:

1. A gemstone tester for characterizing a gemstone, the gemstone tester comprising:
   a detector unit for detecting a plurality of light transmittances through the gemstone, wherein each light transmittance of the plurality of light transmittances is a respective fraction of light of a different wavelength that has passed through the gemstone; and
   a processor configured to:
      determine a first parameter based on a first light transmittance;
      characterize the gemstone as a gemstone type based on the first parameter;
      determine a second parameter based on a ratio of a second and a third light transmittance if the processor cannot determine the gemstone type based on the first parameter; and
      characterize the gemstone based on the second parameter.

2. The gemstone tester of claim 1, further comprising a light source unit for providing the first, second, and third light transmittances at different wavelengths of light, wherein the light source comprises a plurality of light emitting diodes (LEDs) that emit the respective first, second, and third light transmittances, and wherein the processor further comprises controller means for controlling the light source unit to provide the first, second, and third light transmittances in sequence, and wherein the detector unit detects the plurality of light transmittances through the gemstone in sequence.

3. The gemstone tester of claim 2, wherein the light source unit comprises a light source holder that positions the light source unit so that the detector unit can detect the plurality of light transmittances through the gemstone.

4. The gemstone tester of claim 2, wherein the first transmittance is approximately 260 nm light that passes through the gemstone, the second transmittance is approximately 330 nm light that passes through the gemstone, and the third transmittance is approximately 475 nm light that passes through the gemstone.

5. The gemstone tester of claim 2, wherein the gemstone tester is a ruby tester that distinguishes synthetic rubies from natural rubies.

6. The gemstone tester of claim 1, wherein the processor further comprises a storage memory for storing one or more threshold values, wherein the processor characterizes the gemstone by comparing the first parameter with the one or more threshold values.

7. The gemstone tester of claim 1, wherein the processor further comprises a storage memory for storing one or more threshold values, wherein the processor characterizes the gemstone by comparing the first and second parameters with one or more of the threshold values.

8. The gemstone tester of claim 1, wherein the gemstone is one of a group consisting of rubies, diamonds, sapphires, and emeralds.

9. A method of characterizing a gemstone, the method comprising:
   detecting a plurality of light transmittances through the gemstone with a detector unit, wherein each transmittance of the plurality of light transmittances is a respective fraction of light of a different wavelength that has passed through the gemstone;
   determining with a processor a first parameter based on a first light transmittance;
   characterizing the gemstone as a gemstone type based on the first parameter with the processor;
   determining with a processor a second parameter based on a ratio of a second and a third light transmittance if the processor cannot determine the gemstone type based on the first parameter; and
   characterizing the gemstone based on the second parameter with the processor.

10. The method of claim 9, further comprising:
    providing the first, second, and third light transmittances with a light source unit, wherein the light source comprises a plurality of light emitting diodes (LEDs) that each emit light at different wavelengths; and
    controlling the light source unit to provide the first, second, and third light transmittances in sequence, and controlling the detector unit to detect the first, second, and third light transmittances through the gemstone in sequence.

11. The method of claim 10, wherein the first transmittance is approximately 260 nm light that passes through the gemstone, the second transmittance is approximately 330 nm light that passes through the gemstone, and the third transmittance is approximately 475 nm light that passes through the gemstone.

12. The method of claim 10, comprising:
    positioning the light source unit with a light source holder such that the detector unit can detect the plurality of light transmittances through the gemstone.

13. The method of claim 10, wherein the method distinguishes synthetic rubies from natural rubies.

14. The method of claim 9, wherein the step of characterizing the gemstone based on the first parameter with the processor comprises comparing the first parameter with a threshold value stored in a storage memory of the processor.

15. The method of claim 9, wherein the step of characterizing the gemstone comprises comparing the first and second parameters with one or more threshold values stored in a storage memory of the processor.

16. The method of claim 9, wherein the gemstone is one of a group consisting of rubies, diamonds, sapphires, and emeralds.

17. A non-transitory computer readable storage medium having stored thereon computer code for instructing a processor to execute a method of characterizing a gemstone, the method comprising:
    detecting a plurality of light transmittances through the gemstone with a detector unit wherein each transmittance of the plurality of light transmittances is a respective fraction of light of a different wavelength that has passed through the gemstone;
    determining a first parameter based on a first light transmittance;
    characterizing the gemstone as a gemstone type based on the first parameter;
    determining a second parameter based on a ratio of a second and a third light transmittance if the gemstone type cannot be determine based on the first parameter; and characterizing the gemstone based on the second parameter.

18. The non-transitory computer readable storage medium of claim 17, wherein the method further comprises controlling a light source unit to provide the first, second, and third light transmittances in sequence, wherein the light source comprises a plurality of light emitting diodes (LEDs) that each emit light at different wavelengths, and controlling the detector unit to detect the first, second, and third light transmittances through the gemstone in sequence.

19. The non-transitory computer readable storage medium of claim 18, comprising:
   positioning the light source unit with a light source holder such that the detector unit can detect the plurality of light transmittances through the gemstone.

20. The non-transitory computer readable storage medium of claim 17, wherein the step of characterizing the gemstone based on the first parameter with the processor comprises comparing the first parameter with a threshold value stored in a storage memory of the processor.

21. The non-transitory computer readable storage medium of claim 17, wherein the step of characterizing the gemstone comprises comparing the first and second parameters with one or more threshold values stored in a storage memory of the processor.

22. The non-transitory computer readable storage medium of claim 18, wherein the first transmittance is approximately 260 nm light that passes through the gemstone, the second transmittance is approximately 330 nm light that passes through the gemstone, and the third transmittance is approximately 475 nm light that passes through the gemstone.

* * * * *